US012778471B2

(12) United States Patent
Tong et al.

(10) Patent No.: US 12,778,471 B2
(45) Date of Patent: Nov. 3, 2026

(54) GLUCOSE SENSOR

(71) Applicant: Medtronic MiniMed, Inc., Northridge, CA (US)

(72) Inventors: Davy Tong, Thousand Oaks, CA (US); Anuj M. Patel, Northridge, CA (US); Sarnath Chattaraj, Simi Valley, CA (US); Hsi Fusselman, Simi Valley, CA (US); Chia-Hung Chiu, Pasadena, CA (US); Timothy Kwa, Monterey Park, CA (US); Nor Akmaliza Rais, Valencia, CA (US); Michael Weikai Chang, Arcadia, CA (US); Vijaykumar Raorane, Simi Valley, CA (US)

(73) Assignee: Medtronic MiniMed, Inc., Northridge (CA)

( * ) Notice: Subject to any disclaimer, the term of this patent is extended or adjusted under 35 U.S.C. 154(b) by 271 days.

(21) Appl. No.: 17/531,294

(22) Filed: Nov. 19, 2021

(65) Prior Publication Data

US 2023/0157598 A1 May 25, 2023

(51) Int. Cl.
*A61B 5/1495* (2006.01)
*A61B 5/0537* (2021.01)
(Continued)

(52) U.S. Cl.
CPC .......... *A61B 5/1495* (2013.01); *A61B 5/0537* (2013.01); *A61B 5/14532* (2013.01);
(Continued)

(58) Field of Classification Search
CPC . A61B 5/1495; A61B 5/0537; A61B 5/14532; A61B 5/1473; A61B 5/1477; G01N 27/026; G01N 27/08; G01N 33/49
See application file for complete search history.

(56) References Cited

U.S. PATENT DOCUMENTS

| | | | |
|---|---|---|---|
| 9,408,567 | B2 | 8/2016 | Wang et al. |
| 10,321,844 | B2 | 6/2019 | Varsavsky et al. |

(Continued)

FOREIGN PATENT DOCUMENTS

| | | | |
|---|---|---|---|
| GB | 2532726 | A | 6/2016 |
| WO | 2020221841 | A1 | 11/2020 |

OTHER PUBLICATIONS

Mihaela Dinu, "Protective performance of Zr and Cr based silico-oxynitrides used for dental applications by means of potentiodynamic polarization and odd random phase multisine electrochemical impedance spectroscopy", Corrosion Science, vol. 115, 2017, pp. 118-128, ISSN 0010-938X (Year: 2017).*

(Continued)

*Primary Examiner* — Alex M Valvis
*Assistant Examiner* — Grace L Rozanski
(74) *Attorney, Agent, or Firm* — Shumaker & Sieffert, P.A.

(57) ABSTRACT

A method includes monitoring, via a device including an electrochemical cell, an electrical current that is proportional to an impedance of the electrochemical cell, and responsive to determining that the electrical current satisfies a threshold, measuring, via the device, a plurality of impedances of the electrochemical cell corresponding to a plurality of frequencies. The method further includes determining a charge transfer conductance and a solution resistance based on the plurality of impedances at fewer than four of the corresponding plurality of frequencies and determining the presence of electrochemical interference based on the solution resistance and the charge transfer conductance. The method further includes outputting an alert based on the determination of the presence of electrochemical interference.

14 Claims, 9 Drawing Sheets

(51) Int. Cl.

| | |
|---|---|
| ***A61B 5/145*** | (2006.01) |
| ***A61B 5/1473*** | (2006.01) |
| ***A61B 5/1477*** | (2006.01) |
| ***G01N 27/02*** | (2006.01) |
| ***G01N 27/08*** | (2006.01) |
| ***G01N 33/49*** | (2006.01) |

(52) U.S. Cl.

CPC .......... *A61B 5/1473* (2013.01); *A61B 5/1477* (2013.01); *G01N 27/026* (2013.01); *G01N 27/08* (2013.01); *G01N 33/49* (2013.01)

(56) References Cited

U.S. PATENT DOCUMENTS

| | | | | |
|---|---|---|---|---|
| 10,545,113 | B2 | 1/2020 | Davis, Jr. et al. | |
| 2013/0328572 | A1 | 12/2013 | Wang et al. | |
| 2015/0097589 | A1* | 4/2015 | Orazem | G01N 17/04 324/693 |
| 2015/0164371 | A1* | 6/2015 | Varsavsky | A61B 5/14865 600/347 |
| 2015/0164386 | A1 | 6/2015 | Varsavsky et al. | |
| 2016/0345873 | A1 | 12/2016 | Patel et al. | |
| 2020/0025753 | A1* | 1/2020 | Claussen | G01N 33/5438 |
| 2020/0069226 | A1 | 3/2020 | Hahn et al. | |
| 2020/0083541 | A1 | 3/2020 | Swiegers et al. | |
| 2020/0249193 | A1 | 8/2020 | Klemm | |
| 2020/0315504 | A1 | 10/2020 | Lin et al. | |
| 2021/0113111 | A1 | 4/2021 | Varsavsky et al. | |
| 2021/0137420 | A1* | 5/2021 | Masciotti | A61B 5/1451 |
| 2021/0187189 | A1* | 6/2021 | Yuds | A61B 5/021 |
| 2021/0325380 | A1* | 10/2021 | Muthukumar | G01N 33/5438 |
| 2023/0294097 | A1* | 9/2023 | Hasty | C12N 15/63 422/504 |

OTHER PUBLICATIONS

Malkoc et al., "Enhancing Glycemic Control via Detection of Insulin Using Electrochemical Impedance Spectroscopy," Journal of Diabetes Science and Technology, vol. 11, No. 5, Sep. 2017, pp. 930-935.

Jockel et al., "Insulin Depot Formation in Subcutaneous Tissue," Journal of Diabetes Science and Technology, vol. 7, No. 1, Jan. 2013, pp. 227-237.

Thomsen et al., "Visualization of Subcutaneous Insulin Injections by X-Ray Computed Tomography," Physics in Medicine & Biology, vol. 57, No. 21, Oct. 2012, pp. 7197-7203.

Andreescu et al., "A New Electrocatalytic Mechanism for the Oxidation of Phenols at Platinum Electrodes," Electrochemistry Communications, vol. 5, Jul. 9, 2003, pp. 681-688.

Mathiyarasu et al., "Electrochemical Detection of Phenol in Aqueous Solutions," Indian Journal of Chemical Technology, Nov. 2004, pp. 797-803.

Ward et al., "Can Glucose Be Monitored Accurately at the Site of Subcutaneous Insulin Delivery?," Journal of Diabetes Science and Technology, vol. 8, No. 3, May 2014, pp. 568-574.

Norgaard et al., "Performance and Acceptability of a Combined Device for Insulin Infusion and Glucose Sensing in the Home Setting," Journal of Diabetes Science and Technology, vol. 9, No. 2, Mar. 2015, pp. 215-220.

O'Neal et al., "Feasibility of Adjacent Insulin Infusion and Continuous Glucose Monitoring via the Medtronic Combo-Set," Journal of Diabetes Science and Technology, vol. 7, No. 2, Mar. 2013, pp. 381-388.

Brug et al., "The Analysis of electrode impedances complicated by the presence of a constant phase element", Journal of Electroanalytical Chemistry and Interfacial Electrochemistry, vol. 176, No. 1-2, Elsevier, Amsterdam, Netherlands, Sep. 25, 1984, pp. 275-295, DOI: 10.1016/S0022-0728 (84) 20324-1.

Extended Search Report from counterpart European Application No. 22207225.8 dated Apr. 25, 2023, 8 pp.

Communication pursuant to Article 94(3) EPC from counterpart European Application No. 22207225.8 dated Jul. 13, 2026, 4 pp.

* cited by examiner $$Z = R_s + \frac{R_{ct}(1/j\omega C_{dl})}{R_{ct} + (1/j\omega C_{dl})}$$

GLUCOSE SENSOR

TECHNICAL FIELD

This disclosure relates to glucose sensors.

BACKGROUND

Glucose sensors are configured to detect and/or quantify the amount of glucose in a patient's body (e.g., interstitial glucose or possibly blood glucose), which enables patients and medical personnel to monitor physiological conditions within the patient's body. In some examples, it may be beneficial to monitor glucose levels on a continuing basis (e.g., in a diabetic patient). Thus, glucose sensors have been developed for use in obtaining an indication of glucose levels in a diabetic patient. Such indications are useful in monitoring and/or adjusting a treatment regimen, which typically includes administration of insulin to the patient.

A patient can measure their blood glucose (BG) using a BG measurement device (i.e., glucose meter), such as a test strip meter. A continuous glucose measurement system (or a continuous glucose monitor (CGM)) may be configured to determine interstitial glucose; although possible for CGM to determine blood glucose. A hospital hemocue may also be used to determine glucose level. CGMs may be beneficial for patients who desire to take more frequent glucose measurements. Some example CGM systems include subcutaneous (or short-term) sensors and implantable (or long-term) sensors. A CGM system may execute an initialization sequence when the CGM is inserted into a patient. The initialization sequence may speed up sensor equilibration and may allow a CGM system to provide reliable glucose measurements earlier.

SUMMARY

In general, this disclosure describes techniques for determining electrochemical interference of glucose sensors (e.g., a continuous glucose monitor or "CGM") based on one or more electrical parameters. More particularly, this disclosure describes techniques and devices for determining electrical parameters of a glucose sensor in vitro and/or in vivo and identifying and/or detecting electrochemical interference.

In one example, this disclosure describes a method including: monitoring, via a device including an electrochemical cell, an electrical current that is proportional to an impedance of the electrochemical cell; responsive to determining that the electrical current satisfies a threshold, measuring, via the device, a plurality of impedances of the electrochemical cell corresponding to a plurality of frequencies; determining a charge transfer conductance and a solution resistance based on the plurality of impedances at a subset of the corresponding plurality of frequencies; determining the presence of electrochemical interference based on the solution resistance and the charge transfer conductance; and outputting a signal based on the determination of the presence of electrochemical interference.

In another example, this disclosure describes a device including: a glucose monitor; a memory; and one or more processors implemented in circuitry and in communication with the memory, the one or more processors configured to: monitor an electrical current that is proportional to an impedance of the glucose monitor; responsive to determining that the electrical current satisfies a threshold, receive one or more measurements of a plurality of impedances of the glucose monitor corresponding to a plurality of frequencies; determine a charge transfer conductance and a solution resistance of the glucose monitor based on the plurality of impedances at as subset of the corresponding plurality of frequencies; determine the presence of electrochemical interference based on the charge transfer conductance and the solution resistance; and output a signal based on the determination of the presence of electrochemical interference.

In another example, this disclosure describes a non-transitory computer-readable storage medium having stored thereon instructions that, when executed, configure a processor to: monitor, via a device including an electrochemical cell, an electrical current that is proportional to an impedance of the electrochemical cell; responsive to determining that the electrical current satisfies a threshold, receive one or more measurements from the device of a plurality of impedances of the electrochemical cell corresponding to a plurality of frequencies; determine a charge transfer conductance and a solution resistance of the electrochemical cell based on the plurality of impedances at a subset of the corresponding plurality of frequencies; determine the presence of electrochemical interference based on the charge transfer conductance and the solution resistance; and output a signal based on the determination of the presence of electrochemical interference.

The details of one or more examples are set forth in the accompanying drawings and the description below. Other features, objects, and advantages will be apparent from the description and drawings, and from the claims.

DETAILED DESCRIPTION

Figure 1:
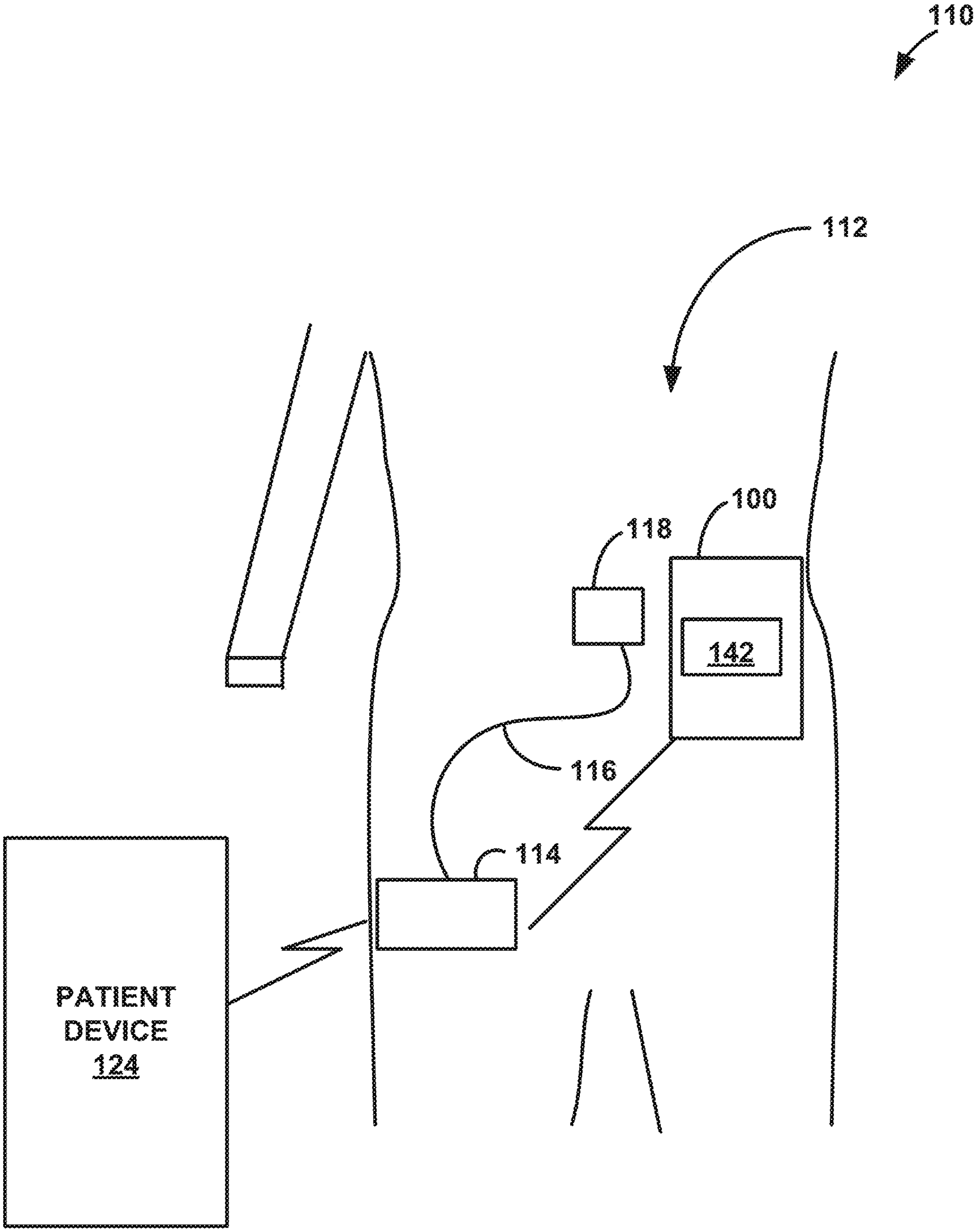
FIG. 1 is a block diagram illustrating an example glucose level management system, in accordance with one or more examples described in this disclosure.

Diabetes patients who use sensor-augmented pump (SAP) therapy may do so by inserting an infusion set and a continuous glucose monitoring (CGM) sensor separately.

The burden of two insertions increases the likelihood of adverse effects of skin penetration, reaction to adhesives, and site loss. Combining the insulin delivery with CGM sensing into a single integrated device addresses these concerns. However, a CGM in close proximity to an infusion catheter may experience electrochemical interference. Electrochemical interference can cause the CGM to provide an inaccurate glucose reading, which may lead to imprecise diagnoses if the readings are used to compute insulin dosage. In examples, disclosed herein, electrochemical impedance spectroscopy (EIS) may be used as a technique to detect when interference is occurring so that action may be taken by the device to ensure patient safety.

A glucose sensor may include an electrochemical cell which may be used to determine a glucose level of a patient. As one example, the glucose sensor may determine interstitial glucose level. The electrochemical cell may apply electrical energy via one or more electrodes displaced within a fluid and/or tissue of a patient, and based on the impedance, determine the glucose level. However, the one or more electrodes may be susceptible to materials within the infused fluid, which may be a commercially available insulin formulation. A bias voltage applied to the electrodes may be needed for the electrodes to function properly. In the presence this bias voltage, the electrodes may cause oxidation of one or more of the substances within the infused fluid. With sufficient prolonged exposure to the substances, the oxidation can lead to deposits and build-up of a thin film on a surface of an electrode. When the interfering substances are oxidized, they can add or subtract from the signal current coming from the glucose, which can lead to inaccurate glucose readings. With prolonged exposure to the substances, the thin film formed on an electrode can cause a permanent change in response characteristics to the glucose. That is, a change in the electrical response of the electrochemical cell to the presence of an analyte, such as glucose. The materials that deposit and form the thin film may be excipients of insulin, e.g., m-cresol, phenol, glycerin, or other materials such as acetaminophen or ascorbic acid. It is important to note that oxidation of interfering compounds alone leads to a temporary interference while thin film deposits on an electrode lead to a permanent change to the electrochemical response of the sensor.

In some examples, a glucose sensor, such as a CGM, and an insulin delivery device, such as an insulin pump, may be packaged together such that the electrode of the glucose sensor may be placed relatively near an insulin delivery site on the patient. Insulin excipient concentration may be greatest nearest the insulin delivery site and may decrease as the excipients diffuse within the patient. In some examples, the higher the concentration of the interfering compounds, the higher the rate of oxidation, and the faster the buildup of a thin film on a glucose sensor electrode causing an increased electrochemical interference. In some examples, even low concentrations of excipients and/or interfering compounds may cause interference followed by a buildup of a thin film on a glucose sensor electrode, e.g., over time, causing progressively increasing electrochemical interference.

The thin film buildup of insulin excipients and/or acetaminophen on a glucose electrode may change the dielectric properties of the electrode and the sensor electrical circuit system, thereby causing the electrochemical interference. Electrochemical interference may confound glucose measurement based on an electrical signal, and the presence of electrochemical interference may not be detectable via the electrical signal alone. For example, a CGM may use a signal current to determine the presence and/or amount of glucose at or near an electrode. Changes in the signal current may be caused by increasing and/or decreasing glucose, electrochemical interference, or both.

EIS may be used as a technique to measure the electrical impedance of the glucose sensor system as a function of frequency of the current and/or voltage. Electrical impedance as a function of frequency measured via EIS may be used, in conjunction with a properly chosen electrical circuit system model, to infer (e.g., determine and/or calculate) dielectric properties of the glucose sensor as well as certain electrical circuit properties of the model. The presence of electrochemical interference may be determined based on the inferred electrical circuit properties of the system model, e.g., solution resistance, charge transfer conductance, double layer capacitance, and the like.

The electrical circuit system model used to determine and/or calculate electrical circuit properties indicative of electrochemical interference based on measured impedance values may be an approximation. For example, the actual physical structure and materials of electrical components of the glucose sensor may be unknown, e.g., at least because of the buildup of the thin film of insulin excipients and/or acetaminophen on one or more electrodes, which may further be a non-homogenous thin film. The accuracy of the approximation may be sensitive to the choice of electrical circuit system model (e.g., the determination/calculation method) and which measured impedance values (e.g., which frequencies and/or frequency ranges) are used in the determination and/or calculation.

In accordance with the techniques of the disclosure, a device including an electrochemical cell may be configured to monitor an electrical current that is proportional to an impedance of the electrochemical cell. The device may be configured to measure a plurality of impedances of the electrochemical cell corresponding to a plurality of frequencies in response to determining that the electrical current satisfies a threshold. The device may be configured to determine a charge transfer conductance and a solution resistance of the electrochemical cell based on the plurality of impedances at a subset of the corresponding plurality of frequencies, e.g., fewer than four of the corresponding plurality of frequencies. The device may be configured to determine the presence of electrochemical interference based on the charge transfer conductance and the solution resistance. The device may be configured to output a signal based on the determination of the presence of electrochemical interference.

In some examples, the device may be configured to determine a solution resistance based on an impedance value corresponding to a relatively high frequency, and to determine the charge transfer conductance based on the solution resistance and an impedance value corresponding to a relatively low frequency. The device may be configured to determine a double layer capacitance based on the solution resistance, the charge transfer conductance, and on an impedance value of the plurality of impedance values corresponding to a frequency at which the impedance phase is substantially negative 90 degrees. In some examples, the device may be configured to determine an amount of permanent electrochemical interference based on the double layer capacitance and/or changes to double layer capacitance over a period of time. In some examples, the device may be configured to determine the cause of the electrochemical interference, e.g., to determine whether the electrochemical interference is caused by insulin excipients, acetaminophen, or some other interfering compound. For example, the device may be configured to determine a Nyquist slope based on the measured impedances, and to determine whether the electrochemical interference is caused by insulin excipients or acetaminophen based on the Nyquist slope and/or a change of the Nyquist slope over a period of time and/or relative to a previously determined Nyquist slope.

FIG. 1 is a block diagram illustrating an example glucose level management system in accordance with one or more examples described in this disclosure. FIG. 1 illustrates system 110 that includes insulin pump 114, tubing 116, infusion set 118, monitoring device 100 (e.g., a glucose level monitoring device comprising a glucose sensor), and patient device 124. The infusion set 118 and monitoring device 100 may be integrated into a single device. Insulin pump 114 may be described as a tethered pump, because tubing 116 tethers insulin pump 114 to infusion set 18. In some examples, rather than utilizing a tethered pump system comprising insulin pump 114, tubing 116, infusion set 118, and/or monitoring device 100, patient 112 may utilize a patch pump. Instead of delivering insulin via tubing and an infusion set, a pump patch may deliver insulin via a cannula extending directly from an insulin pump. In some examples, a glucose sensor may also be integrated into such an insulin patch pump (e.g., a so-called "all-in-one (AIO) insulin pump").

Patient 112 may be diabetic (e.g., Type 1 diabetic or Type 2 diabetic), and therefore, the glucose level in patient 112 may be controlled with delivery of supplemental insulin. For example, patient 112 may not produce sufficient insulin to control the glucose level or the amount of insulin that patient 112 produces may not be sufficient due to insulin resistance that patient 112 may have developed.

To receive the supplemental insulin, patient 112 may carry insulin pump 114 that couples to tubing 116 for delivery of insulin into patient 112. Infusion set 118 may connect to the skin of patient 112 and include a cannula to deliver insulin into patient 112. Monitoring device 100 may also be coupled to patient 112 to measure glucose level in patient 112. Insulin pump 114, tubing 116, infusion set 118, and monitoring device 100 may together form an insulin pump system. One example of the insulin pump system is the MINIMED™ 770G insulin pump system by MEDTRONIC MINIMED, INC. However, other examples of insulin pump systems may be used and the example techniques should not be considered limited to the MINIMED™ 770G insulin pump system. For example, the techniques described in this disclosure may be utilized with any insulin pump and/or glucose monitoring system that includes an in vivo glucose sensor (e.g., a continuous glucose monitor or other in vivo glucose sensor).

Monitoring device 100 may include a sensor that is inserted under the skin of patient 112 (e.g., in vivo), such as near the stomach of patient 112 or in the arm of patient 112 (e.g., subcutaneous connection). The sensor of monitoring device 100 may be configured to measure the interstitial glucose level, which is the glucose found in the fluid between the cells of patient 112. Monitoring device 100 may be configured to continuously or periodically sample the glucose level and rate of change of the glucose level over time.

In one or more examples, insulin pump 114, monitoring device 100, and/or the various components illustrated in FIG. 1, may together form a closed-loop therapy delivery system, which is often referred to as SAP therapy. For example, patient 112 may set a target glucose level, usually measured in units of milligrams per deciliter, on insulin pump 114. Insulin pump 114 may receive the current glucose level from monitoring device 100 and, in response, may increase or decrease the amount of insulin delivered to patient 112. For example, if the current glucose level is higher than the target glucose level, insulin pump 114 may increase the insulin. If the current glucose level is lower than the target glucose level, insulin pump 114 may temporarily cease delivery of the insulin. Insulin pump 114 may be considered as an example of an automated insulin delivery (AID) device. Other examples of AID devices may be possible, and the techniques described in this disclosure may be applicable to other AID devices.

Insulin pump 114 and monitoring device 100 may be configured to operate together to mimic some of the ways in which a healthy pancreas works. Insulin pump 114 may be configured to deliver basal dosages, which are small amounts of insulin released continuously throughout the day. There may be times when glucose levels increase, such as due to eating or some other activity that patient 112 undertakes. Insulin pump 114 may be configured to deliver bolus dosages on demand in association with food intake or to correct an undesirably high glucose level in the bloodstream. In one or more examples, if the glucose level rises above a target level, then insulin pump 114 may deliver a bolus dosage to address the increase in glucose level. Insulin pump 114 may be configured to compute basal and bolus dosages and deliver the basal and bolus dosages accordingly. For instance, insulin pump 114 may determine the amount of a basal dosage to deliver continuously and then determine the amount of a bolus dosage to deliver to reduce glucose level in response to an increase in glucose level due to eating or some other event.

Accordingly, in some examples, monitoring device 100 may sample glucose levels for determining rate of change in glucose level over time. Monitoring device 100 may output the glucose level to insulin pump 114 (e.g., through a wireless link connection like Bluetooth). Insulin pump 114 may compare the glucose level to a target glucose level (e.g., as set by patient 112 or a clinician) and adjust the insulin dosage based on the comparison. In some examples, insulin pump 114 may adjust insulin delivery based on a predicted glucose level (e.g., where glucose level is expected to be in the next 30 minutes).

As described above, patient 112 or a clinician may set one or more target glucose levels on insulin pump 114. There may be various ways in which patient 112 or the clinician may set a target glucose level on insulin pump 114. As one example, patient 112 or the clinician may utilize patient device 124 to communicate with insulin pump 114. Examples of patient device 124 include mobile devices, such as smartphones, tablet computers, laptop computers, and the like. In some examples, patient device 124 may be a special programmer or controller (e.g., a dedicated remote control device) for insulin pump 114. Although FIG. 1 illustrates one patient device 124, in some examples, there may be a plurality of patient devices. For instance, system 110 may include a mobile device and a dedicated wireless controller, each of which is an example of patient device 124. For ease of description only, the example techniques are described with respect to patient device 124 with the understanding that patient device 124 may be one or more patient devices.

Patient device 124 may also be configured to interface with monitoring device 100. As one example, patient device 124 may receive information from monitoring device 100 through insulin pump 114, where insulin pump 114 relays the information between patient device 124 and monitoring device 100. As another example, patient device 124 may receive information (e.g., glucose level or rate of change of glucose level) directly from monitoring device 100 (e.g., through a wireless link).

In one or more examples, patient device 124 may comprise a user interface with which patient 112 or the clinician may control insulin pump 114. For example, patient device 124 may comprise a touchscreen that allows patient 112 or the clinician to enter a target glucose level. Additionally or alternatively, patient device 124 may comprise a display device that outputs the current and/or past glucose level. In some examples, patient device 124 may output notifications to patient 112, such as notifications if the glucose level is too high or too low, as well as notifications regarding any action that patient 112 needs to take.

In some examples, monitoring device 100 and insulin pump 114 of an insulin pump system and/or infusion set 118 may be packaged together such that an electrochemical cell or working electrode 160 (FIG. 3A) of the glucose sensor may be placed relatively near an insulin delivery site on the patient. Insulin excipients from insulin doses or boluses may cause the excipients to be oxidized and possibly lead to deposits and build up a thin film on the surface of the electrode of monitoring device 100, as described above, causing electrochemical interference and a change in the electrical parameters of the glucose sensor.

In accordance with the techniques, device, and systems disclosed herein, a monitoring device 100 may be configured to determine the presence of electrochemical interference, and in some examples, determine a cause of the electrochemical interference. Monitoring device 100 may be configured to determine one or more electrical parameters of an electrochemical cell of monitoring device 100. In some examples, monitoring device 100 may include an interference detection unit 142 configured to determine one or more electrical parameters of an electrochemical cell of monitoring device 100 and the presence and/or cause of electrochemical interference, e.g., as further described below with reference to FIG. 2. In some examples, patient device 124 or another device may include interference detection unit 142, in addition to or instead of monitoring device 100. Electrical parameters may include, for example, a voltage, an electrical current (e.g., iSig 157 illustrated in FIG. 3A), or an impedance. In general, the electrical current (iSig 157) flowing through the sensing (e.g., working) electrode of monitoring device 100 is indicative of the blood glucose level in the patient's interstitial fluid. In some examples, the sensing electrode may be part of an electrochemical cell configured to measure the voltage, iSig, or impedances.

For example, monitoring device 100 may be configured monitor an electrical current that is proportional to an impedance of the electrochemical cell and to measure a plurality of impedances of the electrochemical cell corresponding to a plurality of frequencies, e.g., responsive to determining that the electrical current satisfies a threshold. In other words, as described in more detail, monitoring device 100 may be configured to perform a diagnostic test upon an electrical parameter, e.g., iSig, satisfying a threshold, such as being too low or too high relative to a predetermined expected value range. Monitoring device 100 may be further configured to determine a charge transfer conductance and a solution resistance of the electrochemical cell based on the plurality of impedances at a subset, e.g., fewer than four, of the corresponding plurality of frequencies, determine the presence of electrochemical interference based on the charge transfer conductance and the solution resistance, and output a signal, e.g., to patient device 124, insulin pump 114, or any other suitable device, based on the determination of the presence of electrochemical interference. The signal may be information indicative of the presence and/or amount of electrochemical interference, and another device (e.g., patient device 124, or any other suitable device, may output an alert based on the signal. In some examples, monitoring device 100 may be further configured to determine a Nyquist slope and determine whether the electrochemical interference is caused by insulin excipients or acetaminophen based on the Nyquist slope.

Figure 2:
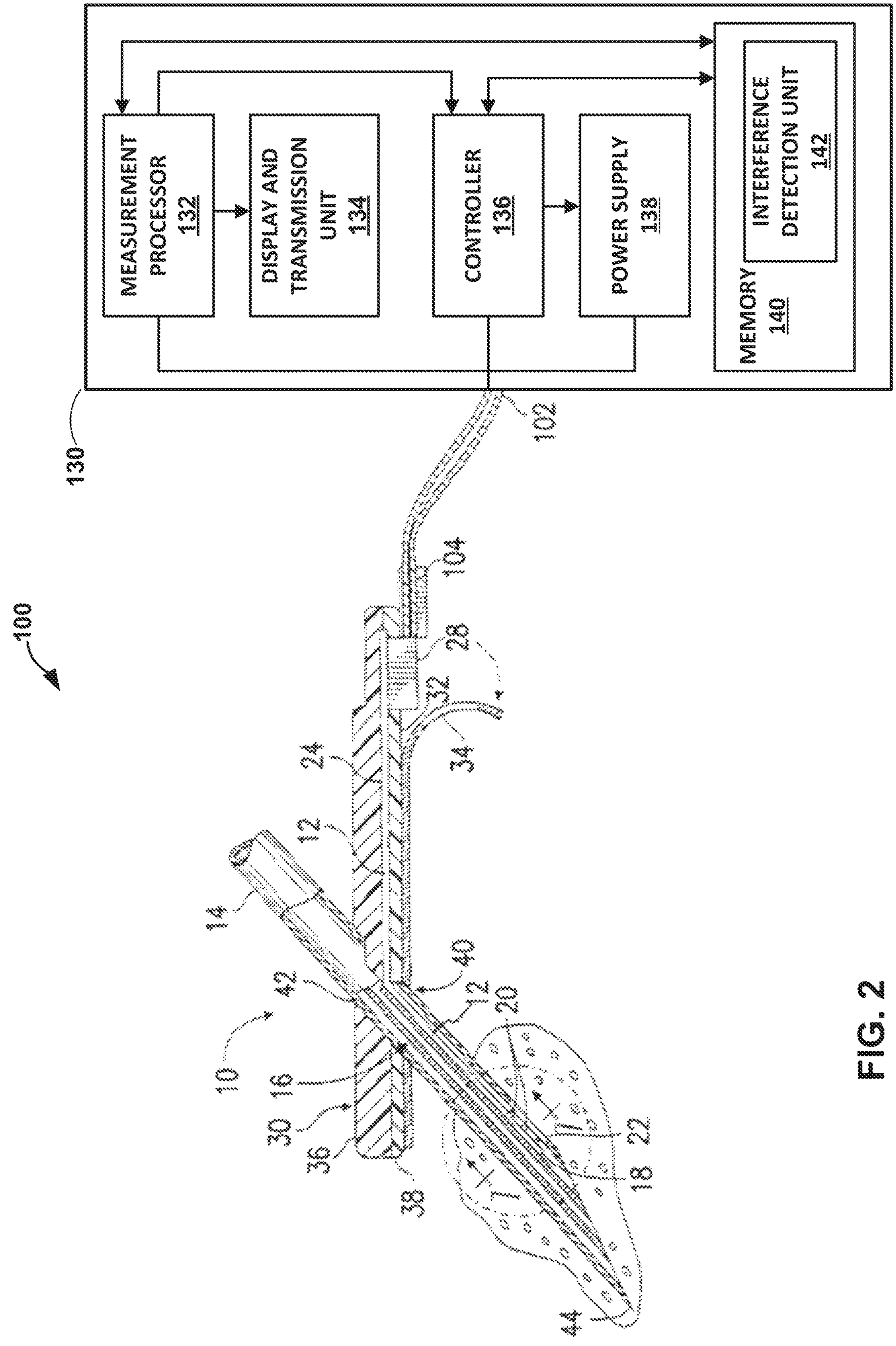
FIG. 2 is a block diagram illustrating an example glucose sensor, in accordance with one or more examples described in this disclosure.

FIG. 2 is a block diagram illustrating monitoring device 100 in more detail. In particular, FIG. 2 is a perspective view of a subcutaneous sensor insertion set and a block diagram of sensor electronics device 130 of monitoring device 100 according to an example of the disclosure. As illustrated in FIG. 2, subcutaneous sensor set 10 is provided for subcutaneous placement of an active portion of flexible glucose sensor 12 at a selected site in the body of patient 112. The subcutaneous or percutaneous portion of sensor set 10 includes a hollow, slotted insertion needle 14, and cannula 16. Needle 14 is used to facilitate quick and easy subcutaneous placement of cannula 16 at the subcutaneous insertion site. Inside cannula 16 is glucose sensing portion 18 of glucose sensor 12, which is configured to expose one or more glucose sensor electrodes 20 to the bodily fluids (e.g., blood or interstitial fluid) of patient 112 through window 22 formed in cannula 16. In one example, one or more glucose sensor electrodes 20 may include a counter electrode 156, a reference electrode 158, and one or more working electrodes 160. Examples of the counter electrode 156, reference electrode 158, and working electrode(s) 160 are described in more detail with respect to FIG. 3A. After insertion, insertion needle 14 is withdrawn to leave cannula 16 with glucose sensing portion 18 and glucose sensor electrodes 20 in place at the selected insertion site.

In some examples, subcutaneous sensor set 10 facilitates accurate placement of flexible thin film electrochemical glucose sensor 12 of the type used for monitoring specific blood parameters representative of a condition of patient 112. Glucose sensor 12 monitors glucose levels in the body, and may be used in conjunction with automated or semi-automated medication infusion pumps of the external or implantable type as described above to control delivery of insulin to patient 112.

Examples of flexible electrochemical glucose sensor 12 are constructed in accordance with thin film mask techniques to include elongated thin film conductors embedded or encased between layers of a selected insulative material such as polyimide film or sheet, and membranes. Glucose sensor electrodes 20 at a tip end of glucose sensing portion 18 are exposed through one of the insulative layers for direct contact with patient blood or other body fluids, when glucose sensing portion 18 (or active portion) of glucose sensor 12 is subcutaneously placed at an insertion site. Glucose sensing portion 18 is joined to connection portion 24 that terminates in conductive contact pads, or the like, which are also exposed through one of the insulative layers. In other examples, other types of implantable sensors, such as chemical based, optical based, or the like, may be used.

Connection portion 24 and the contact pads are generally adapted for a direct wired electrical connection to a suitable monitor or sensor electronics device 130 for monitoring a condition of patient 112 in response to signals derived from glucose sensor electrodes 20. Connection portion 24 may be conveniently connected electrically to the monitor or sensor electronics device 130 or by connector block 28. Thus, in accordance with examples of the disclosure, subcutaneous sensor sets 10 may be configured or formed to work with either a wired or a wireless characteristic monitor system.

Glucose sensor electrodes 20 may be used in a variety of sensing applications and may be configured in a variety of ways. For example, glucose sensor electrodes 20 may be used in physiological parameter sensing applications in which some type of biomolecule is used as a catalytic agent. For example, glucose sensor electrodes 20 may be used in a glucose and oxygen sensor having a glucose oxidase (GOx) enzyme catalyzing a reaction with glucose sensor electrodes 20. Glucose sensor electrodes 20, along with a biomolecule or some other catalytic agent, may be placed in a human body in a vascular or non-vascular environment. For example, glucose sensor electrodes 20 and biomolecules may be placed in a vein and be subjected to a blood stream, or may be placed in a subcutaneous or peritoneal region of the human body.

Sensor electronics device 130 may include measurement processor 132, display and transmission unit 134, controller 136, power supply 138, and memory 140. Sensor electronics device 130 may be coupled to the sensor set 10 by cable 102 through a connector that is electrically coupled to connector block 28 of connection portion 24. In other examples, the cable may be omitted and sensor electronics device 130 may include an appropriate connector for direct connection to connection portion 104 of sensor set 10. Sensor set 10 may be modified to have connector portion 104 positioned at a different location, e.g., on top of the sensor set to facilitate placement of sensor electronics device 130 over the sensor set.

In examples of the disclosure, measurement processor 132, display and transmission unit 134, and controller 136 may be formed as separate semiconductor chips. However, other examples may combine measurement processor 132, display and transmission unit 134, and controller 136 into a single or multiple customized semiconductor chips. In general, measurement processor 132 may be configured to receive a current, voltage, and/or impedance from glucose sensor electrodes 20. Glucose sensor electrodes 20 may generate a sensor signal indicative of a concentration of a physiological characteristic being measured. For example, the sensor signal may be indicative of a glucose reading. The sensor signal may be measured at a working electrode 160 of glucose sensor electrodes 20. In an example of the disclosure, the sensor signal may be a current (e.g., iSig) measured at the working electrode 160. In another example of the disclosure, the sensor signal may be a voltage measured at the working electrode 160 of glucose sensor electrodes 20.

Electrical parameters of monitoring device 100 may include impedance parameters. An example of an impedance parameter may include EIS. EIS may provide additional information in the form of sensor impedance and impedance-related parameters at a plurality of different frequencies. Moreover, for certain ranges of frequencies, impedance and/or impedance-related data may indicate electrochemical interference. Determination of electrochemical interference enables correction of the electrochemical interference to improve the reliability of the sensor glucose value and to assess the condition, health, age, and efficiency of the sensor. For example, analysis of impedance data in the context of an appropriate electrical circuit model provides information on the presence of electrochemical interference of a sensor of monitoring device 100 and information on a cause of the electrochemical interference when the interference is present.

Measurement processor 132 receives the sensor signal (e.g., a measured current, voltage, and/or impedance) after the sensor signal is measured at glucose sensor electrodes 20 (e.g., a working electrode 160). Measurement processor 132 may receive the sensor signal and calibrate the sensor signal utilizing reference values. For example, measurement processor 132 may calibrate the sensor signal utilizing reference values based on a known analyte quantity, e.g., a zero glucose measurement to determine a baseline sensor signal. In some examples, changes to the sensor over time may change the responsivity of the glucose sensor, changing the sensor signal and glucose measurement accuracy. Measurement processor 132 may utilize the reference values to adjust for changes over time. In some examples, monitoring device 100 may update and or adjust the reference values, e.g., using EIS data or other data. In an example of the disclosure, the reference values are stored in a reference memory (e.g., memory 140) and provided to measurement processor 132. Based on the sensor signals and the reference values, measurement processor 132 may determine a glucose measurement. Measurement processor 132 store the glucose measurements in memory 140. The sensor measurements may be sent to display and transmission unit 134 to be either displayed on a display in a housing of monitoring device 100 or transmitted to an external device.

Memory 140 may be any type of memory device and may be configured to store glucose measurements produced by measurement processor 132, reference values used to determine glucose measurements from sensor signals, or other data used and/or produced by measurement processor 132 and/or controller 136. In some examples, memory 140 may further store software and/or firmware that is executable by measurement processor 132 and/or controller 136.

Sensor electronics device 130 may be a monitor which includes a display to display physiological characteristics readings. In some examples, sensor electronics device 130 may be remote from sensor set 10 and communicatively connected to sensor set 10, e.g., via a wired or wireless connection. For example, sensor electronics device 130 may also be installed in a desktop computer, a pager, a television including communications capabilities, a laptop computer, a server, a network computer, a personal digital assistant (PDA), a portable telephone including computer functions, an infusion pump including a display, a glucose sensor including a display, and/or a combination infusion pump/glucose sensor. Sensor electronics device 130 may be housed in a mobile phone, a network device, a home network device, or an appliance connected to a home network.

Power supply 138 may be a battery. The battery can include three series silver oxide 357 battery cells. In other examples, different battery chemistries may be utilized, such as lithium based chemistries, alkaline batteries, nickel metalhydride, or the like, and a different number of batteries may be used. Sensor electronics device 130 provides power to the sensor set 10 via power supply 138 through cable 102 and cable connector 104.

Controller 136 may be a processor, digital signal processors (DSPs), application specific integrated circuits (ASICs), field programmable gate arrays (FPGAs), or any other equivalent integrated or discrete logic circuitry. In some examples controller 136 may be configured to cause a specific voltage or current to be output to glucose sensor electrodes 20. Glucose sensor electrodes 20 may receive the voltage level or value. In an example of the disclosure, a counter electrode 156 of glucose sensor electrodes 20 may receive the reference voltage from power supply 138. The application of the voltage level causes glucose sensor electrodes 20 to create a sensor signal (e.g., a current through a working electrode 160) indicative of a concentration of a physiological characteristic being measured (e.g., blood glucose).

Figure 3A:
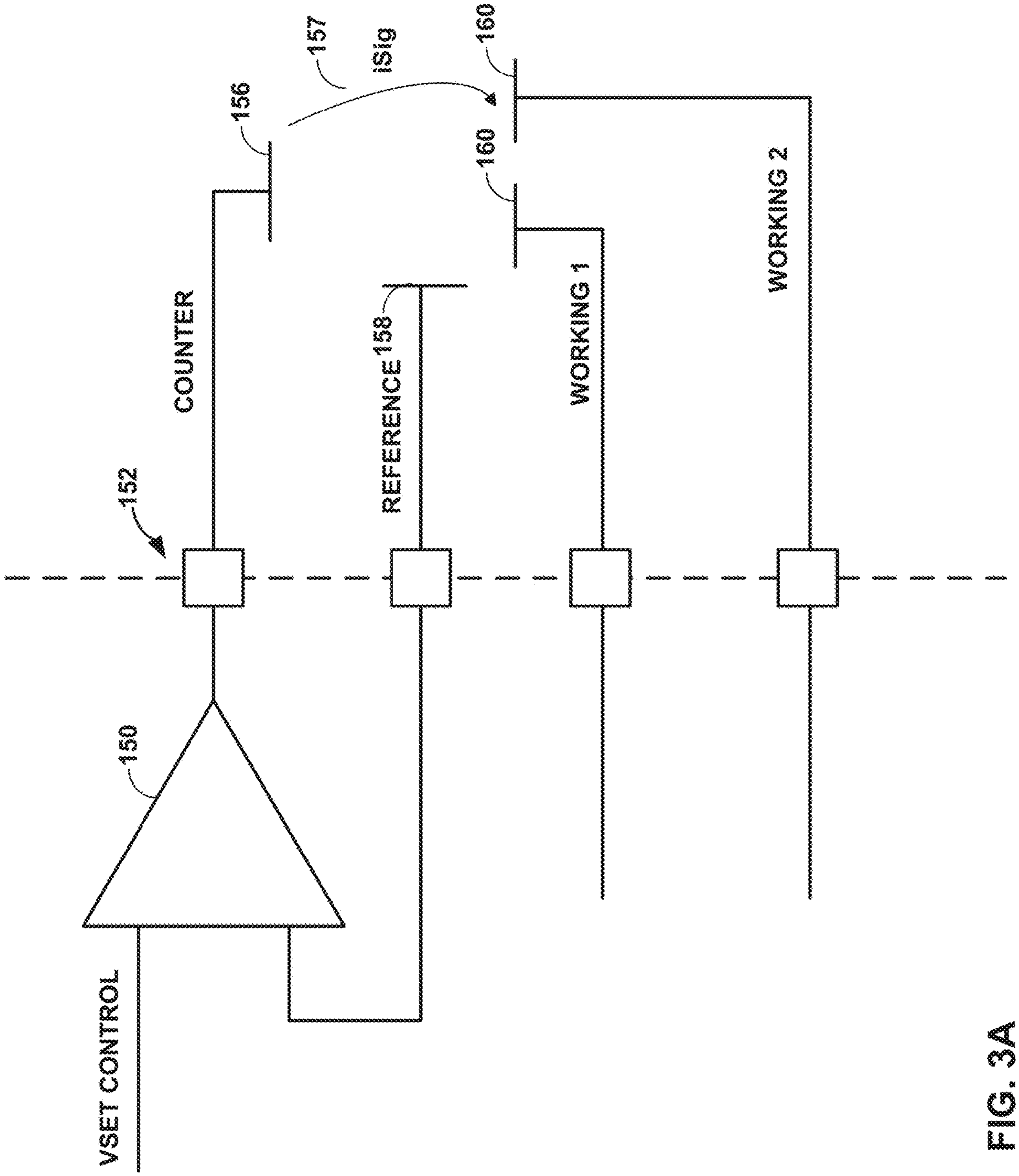
FIG. 3A is a block diagram illustrating example sensor electrodes and a voltage being applied to the sensor electrodes.

FIG. 3A is a block diagram illustrating example sensor electrodes and a bias voltage being applied to the sensor electrodes according to an example of the disclosure. In the examples shown, example sensor electrodes include counter electrode 156, reference electrode 158, and working electrodes 160, which may be examples of glucose sensor electrodes 20 and may be used in a glucose and oxygen sensor having a glucose oxidase (GOx) enzyme catalyzing a reaction with electrodes 156, 158, 160. In the example in FIG. 3A, an operational amplifier (op amp) 150 or other servo controlled device may connect to glucose sensor electrodes 20 through a circuit/electrode interface 152. Op amp 150, utilizing feedback through glucose sensor electrodes 20, attempts to maintain a prescribed voltage between reference electrode 158 and a working electrode 160 (e.g., VSET) by adjusting the voltage at counter electrode 156. In some examples, the voltage at reference electrode 158 is 850 mv.

Current 157 (iSig) may then flow from a counter electrode 156 to a working electrode 160. Counter electrode 156 balances the chemical reaction that is occurring at working electrode 160. Measurement processor 132 of FIG. 2 may measure current 157 to determine the electrochemical reaction between glucose sensor electrodes 20. The circuitry disclosed in FIG. 3A may be utilized in a long-term or implantable sensor or may be utilized in a short-term or subcutaneous sensor.

Returning to FIG. 2, as discussed above, due to electrochemical interference, monitoring device 100 may provide inaccurate readings to patient 112. As such, interference detection unit 142 may be configured to detect electrochemical interference and a cause of electrochemical interference. Either of measurement processor 132 and/or controller 136 may be configured to execute interference detection unit 142. Although interference detection unit 142 is illustrated as software that executes on measurement processor 132 and/or controller 136, in some examples, interference detection unit 142 may be fixed-function circuitry that is formed within monitoring device 100 (e.g., within measurement processor 132 and/or controller 136 or independent of measurement processor 132 and/or controller 136). In some examples, inference detection unit 142 may be firmware that measurement processor 132 and/or controller 136 execute.

In accordance with the techniques of this disclosure, interference detection unit 142 is configured to monitor an electrical parameter of the electrical chemical cell of monitoring device 100, e.g., an electrical current that is proportional to the impedance of the electrochemical cell such as iSig 157. For example, measurement processor 132 may provide a sensor signal to controller device 150. In one example, the sensor signal is a current (iSig 157) through a working electrode 160 of glucose sensor electrodes 20. Controller 136 may accumulate current values over a period of time and may calculate a rate of change of the current values. For example, controller 136 may calculate the slope of a plot of the current (e.g., iSig 157).

In other examples, controller 136 may accumulate and measure changes in EIS (real and imaginary impedance at different frequencies), voltage at a counter electrode 156, and/or current through a background electrode. A background electrode is similar to a working electrode 160, but does not include Gox layer for breaking down and sensing glucose. Like current through a working electrode 160, larger slopes/changes in these other sensor signals may indicate a need for a higher VSET, whole lower slopes/changes in these other sensor signals may indicate a need for a lower VSET at the working electrode 160. Interference detection unit 142 may be configured to monitor EIS, voltage, and/or current through a background electrode similar to monitoring iSig 157 as described herein.

In some examples, sensor electronics device 130 may monitor fewer than all of the electrical parameters of monitoring device 100, e.g., sensor electronics device 130 may monitor just iSig 157 and audit other electrical parameters at certain points in time or in response to an occurrence such as a monitored parameter (e.g., iSig 157) satisfying a threshold. Interference detection unit 142 is further configured to measure a plurality of impedances of the electrochemical cell, e.g., via EIS, if iSig 157 satisfies a threshold.

For example, a spike in iSig 157 may indicate a rise in glucose, or a spike in iSig 157 may indicate a rise in interferents such as insulin excipients. The threshold value may be predetermined, at least initially, and stored in memory 140, and may be a value at which other electrical parameters may be measured/audited to determine the presence of electrochemical interference. The threshold value may be adjusted over time, e.g., so as to compensate for changes to the causes of electrochemical interference over time such as changes to a thin film of insulin excipients deposited on an electrode of the electrochemical cell, e.g., any of electrodes 156, 158, 160. The threshold value may be predetermined, adjusted, or determined based on previous iSig 157 measurements, e.g., for comparison to determine if there is a change to an average value of an iSig 157 spike, or based on any other information indicating an iSig 157 value at which a diagnostic test should be performed to determine whether electrochemical interference is present and/or has changed. In other words, sensor electronics device 130 may monitor iSig 157 and electrical parameters (e.g. EIS) to determine whether a spike in iSig 157 is due to glucose, and/or electrochemical interference.

Interference detection unit 142 may utilize electrical model components calculated based on impedance measurements at a plurality of frequencies to determine the presence and, in some examples, the cause of electrochemical interference. For example, interference detection unit 142 may determine a charge transfer conductance, a solution resistance, and a double layer capacitance based on an electrical circuit model representing the electrical chemical cell, e.g., electrical circuit model 400 illustrated and described below with reference to FIG. 4.

Electrical circuit model components may be idealized components, e.g., relating to simplified, idealized electrical components such as uniform resistors, capacitors, and inductors. The electrical phenomena occurring within an electrochemical cell may vary from that of an electrical circuit model because the electrical components of the electrical chemical cell may not be, and may not behave, as simple resistors, capacitors, and inductors. For example, nonuniformities in a fluid (e.g., interstitial fluid) may cause the resistance of the fluid to vary spatially, temporally, and at different electrical frequencies (e.g., spectrally, or according to a spectral response). Similarly, a thin film buildup on an electrode of the electrical cell may not be spatially, temporally, and at different electrical frequencies, e.g., modifying the electrode to be a non-uniform electrode. As such, electrical circuit model components such as charge transfer conductance, solution resistance, and double layer capacitance are simplifications of actual electrical phenomena occurring within the electrochemical cell. The actual electrical circuit model components of the electrochemical cell may be prohibitively complex to directly measure, and the accuracy of calculated electrical circuit model components in representing the actual electrical phenomena of the electrochemical cell depends on how those components are calculated, which depends on, or is informed by, the electrical circuit model chosen. In turn, the accuracy of determining whether electrochemical interference and a cause of electrochemical interference depends on the accuracy of the calculated electrical circuit model components of the chosen electrical circuit model.

Figure 4:
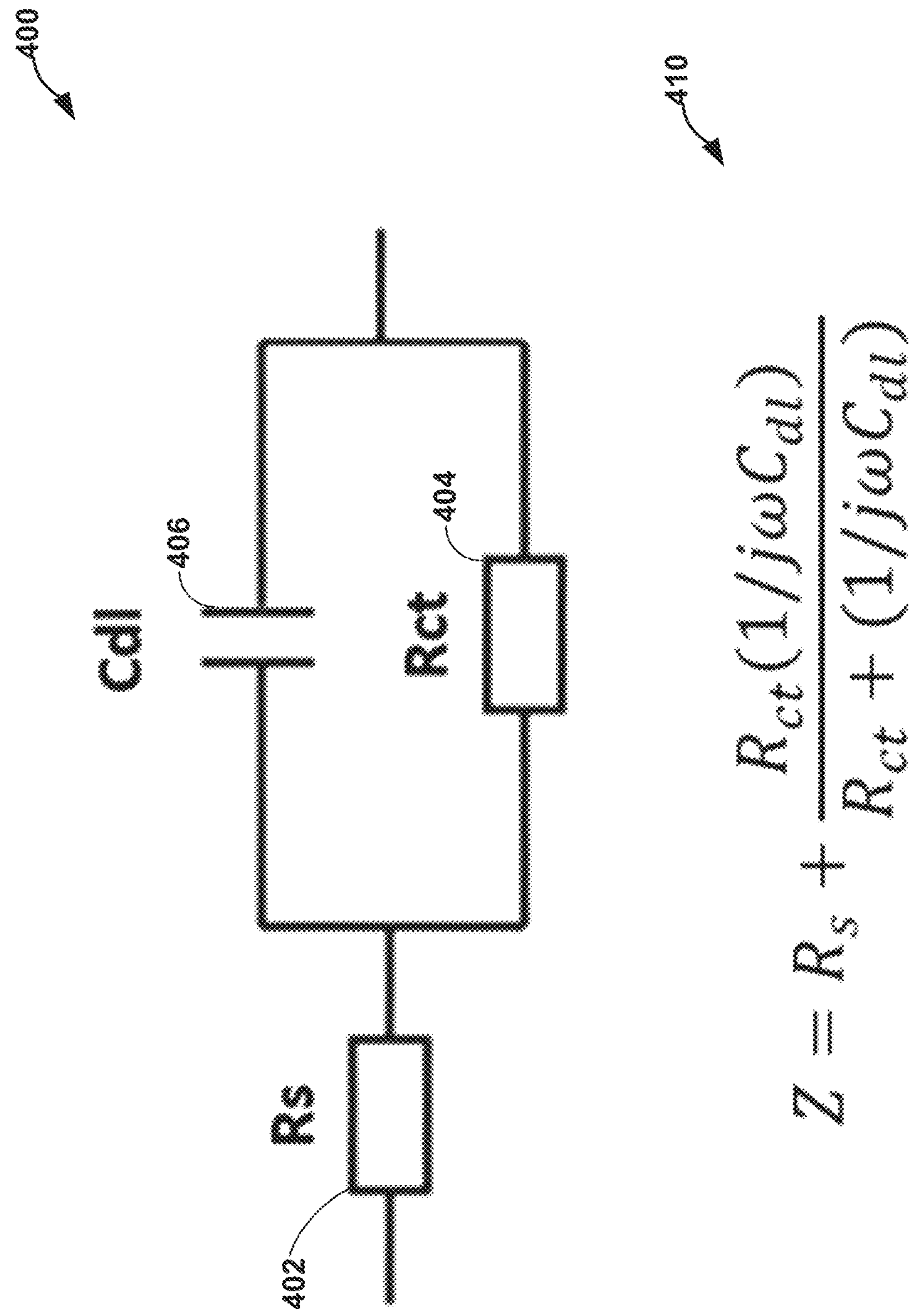
FIG. 4 is a circuit diagram illustrating an example electrical circuit model of an electrochemical cell of a monitoring device.

In some examples, interference unit 142 is configured to determine component values for components of an electrical circuit model based on an electrical circuit model of the electrochemical cell that does not include either of a constant phase element or a Warburg impedance. For example, interference unit 142 may be configured to calculated each of the solution resistance, charge transfer conductance, and double layer capacitance as non-constant phase elements. In some examples, interference unit 142 may be configured to calculate electrical circuit model components based on an electrical circuit model in which the solution resistance is in series with a parallel combination of the double layer capacitance and a charge transfer resistance (e.g., as illustrated in FIG. 4). The charge transfer resistance is proportional to the inverse of the charge transfer conductance.

Interference unit 142 is further configured to determine electrical circuit model components, e.g., a charge transfer conductance, a solution resistance, and/or a double layer capacitance based on the measured impedances at fewer than four frequencies. As described below, based on an electrical circuit model such as electrical circuit model 400, interference unit 142 may determine the charge transfer conductance based on impedance data at a low frequency (e.g., using equation 1 below) and the solution resistance, which interference unit 142 may determine based on impedance data at a high frequency as described below. Interference unit 142 may determine the double layer capacitance based on impedance data at a frequency at which the impedance has a corresponding to phase that is closest to negative 90 degrees (e.g., using equation 2 below), which may be the impedance at the low frequency used to determine the charge transfer conductance. In other words, interference unit 142 may be configured to determine a charge transfer conductance, a solution resistance, and/or a double layer capacitance based on measured impedances at two frequencies, and may use more impedance data (e.g., at other frequencies) to determine such electrical circuit model components, e.g., to reduce uncertainty in the calculated electrical circuit model components.

For example, interference unit 142 may be configured to determine the solution resistance based on an impedance value corresponding to a relatively high frequency, e.g., a measured impedance value at a frequency that is greater than 500 Hz, or is at least 1 kilohertz (kHz) and less than or equal to 8 kHz. Interference unit 142 may be configured to determine the charge transfer conductance based on the solution resistance and based on an impedance value of the plurality of impedance values corresponding to a relatively low frequency, e.g., at least 0.1 Hz and less than or equal to 8 kHz, or at least 0.1 Hz and less than or equal to 100 Hz. Interference unit 142 may be configured to determine the double layer capacitance based on the solution resistance, the charge transfer conductance, and based on an impedance value of the plurality of impedance values at which the impedance phase is substantially negative 90 degrees. Interference unit 142 is further configured to determine an amount of electrochemical interference based on the double layer capacitance.

In some examples, interference unit 142 is configured to determine changes in electrochemical interference over time. For example, interference unit 142 may be configured to measure a first plurality of impedances at a first time, and determine a first charge transfer conductance and a first solution resistance of the electrochemical cell based on the first plurality of impedances at fewer than four of the corresponding plurality of frequencies, and to determine a first double layer capacitance based on the first solution resistance and charge transfer conductance and on the impedance value of the first plurality of impedance values corresponding to a frequency at which the impedance phase is substantially negative 90 degrees (e.g., negative 50 to 40 degrees). Interference unit 142 may be configured to then measure a second plurality of impedances at a second time, and determine a second charge transfer conductance and a second solution resistance of the electrochemical cell based on the second plurality of impedances at fewer than four of the corresponding plurality of frequencies, and to determine a second double layer capacitance based on the second solution resistance and charge transfer conductance and on the impedance value of the second plurality of impedance values corresponding to a frequency at which the impedance phase is substantially negative 90 degrees. Interference unit 142 may be configured to determine both a first amount of electrochemical interference at the first time based on the first double layer capacitance, and a second amount of electrochemical interference at the second time based on the second double layer capacitance. Interference unit 142 may be configured to further track the amount of electrochemical interference as a function of time, and store the results, e.g., in memory 140.

In some examples, interference unit 142 is further configured to determine a cause of electrochemical interference. For example, interference unit 142 may be configured to determine a Nyquist slope, e.g., based on the measured impedances at the plurality of frequencies, and to determine whether the electrochemical interference is caused by insulin excipients or acetaminophen. Acetaminophen may not cause a change to an electrode of monitoring device 100, but rather may cause a change in the electrical properties of the solution (e.g., the analyte or interstitial fluid), e.g., similar to glucose. In other words, the presence of both glucose and acetaminophen may be detectable by monitoring device 100, e.g., via iSig 157, but glucose and acetaminophen may not be distinguishable from each other based on iSig 157 alone. The cause of electrochemical interference due to acetaminophen may be an electrochemical interference of the analyte, e.g., the interstitial fluid, rather than a change to an electrode of the electrochemical cell of monitoring device 100. As such, electrochemical interference due to acetaminophen may not be discernable based on changing electrical circuit model components of the electrochemical cell, e.g., the charge transfer conductance, solution resistance, and double layer capacitance.

An increased concentration of glucose, e.g., in the interstitial fluid, may cause the Nyquist slope, e.g., determined via EIS data measured by monitoring device 100, to increase, whereas an increased concentration of acetaminophen may cause the Nyquist slope to decrease. Interference unit 142 may track and compare Nyquist slopes determined from EIS data (e.g., impedances as a plurality of frequencies) measured at different times, and may determine whether an iSig 157 signal, event, spike, change, feature, or the like, is due to acetaminophen based on a Nyquist slope, a change in Nyquist slope over time, and/or a rate of change of Nyquist slope. In some examples, interference unit 142 may be configured to determine that electrochemical interference is caused by acetaminophen based on Nyquist slope, iSig 157, and a lack of change in the electrical circuit model components (e.g., a lack of charge transfer conductance, solution resistance, and double layer capacitance indicating a lack of a thin film buildup or changes to an electrode). In some examples, interference unit 142 may be configured to determine that electrochemical interference is caused by acetaminophen, insulin excipient, or both, based on any or all of Nyquist slope, Nyquist slope change, rate of Nyquist slope change, iSig 157, and either a change or lack of change in the electrical circuit model components.

Figure 3B:
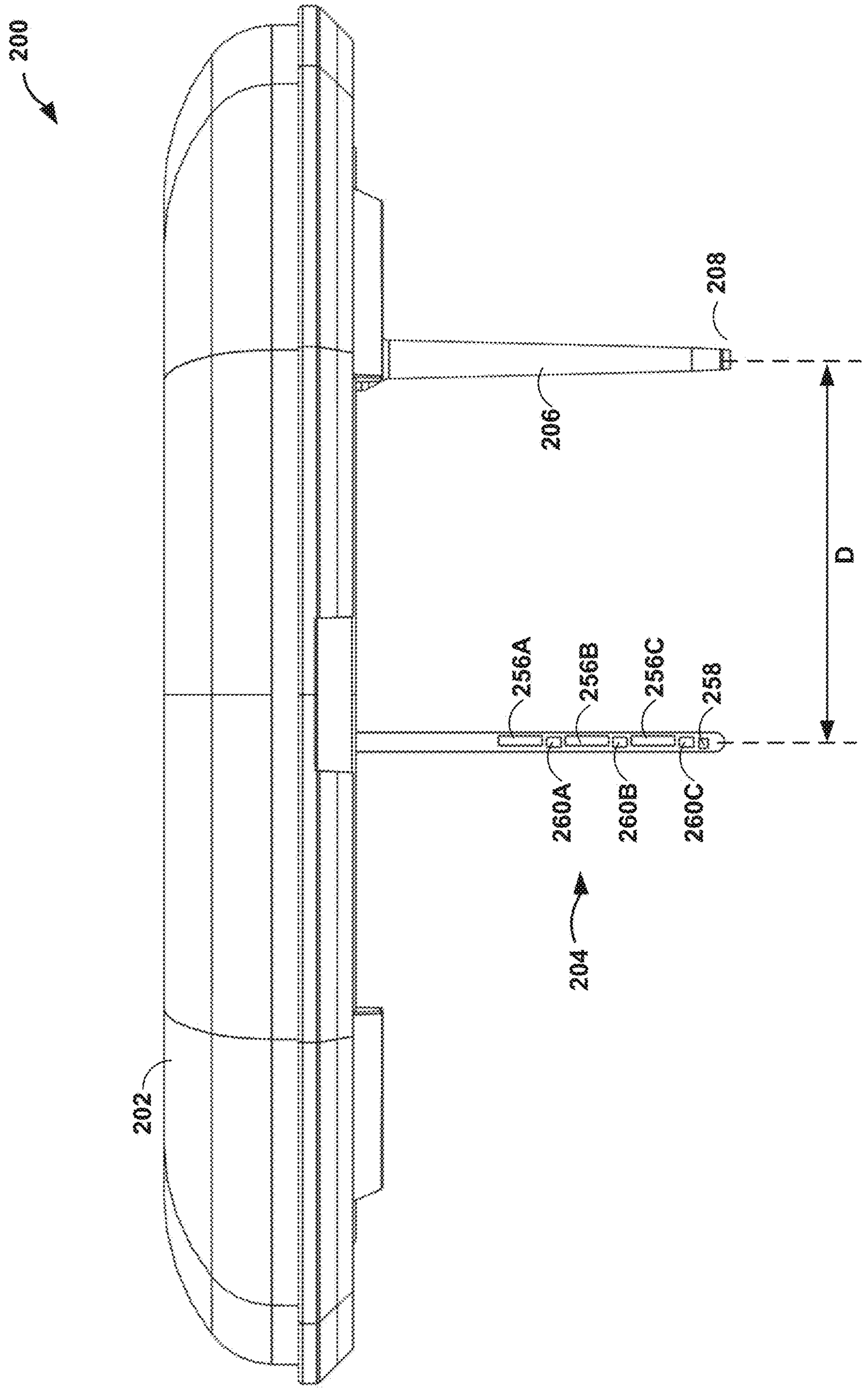
FIG. 3B is a cross-sectional view of an example medical device including a monitoring device and insulin pump.

FIG. 3B is a cross-sectional view of an example medical device 200 including a monitoring device and insulin pump. In the example shown, medical device 200 includes a CGM and an insulin delivery device packaged together such that the electrode of the glucose sensor is placed relatively near an insulin delivery site on the patient. Medical device 200 may inserted into patient 112 a single time and include both insulin delivery and glucose monitoring functionalities, e.g., so that patient 112 doesn't need to have two different devices inserted, e.g., two different insertions. In the example shown, medical device 200 includes housing 202, sensing portion 204, and delivery lumen 206.

Housing 202 may be configured to house a CGM (not shown) and insulin pump (not shown), such that sensing portion 204 and delivery lumen 206 may be inserted into patient 112 and separated laterally by a distance D.

Sensing portion 204 may include sensor electrodes 256, 258, and 260. In the example shown, sensing portion 204 includes three counter electrodes 256A, 256B, and 256C (collectively referred to as "counter electrodes 256"), and three working electrodes 260A, 260B, and 260C, (collectively referred to as "working electrodes 260"), which may form three glucose sensors, e.g., working-counter electrode pairs providing three separate sensor signals (iSigs). Sensing portion 204 also includes reference electrode 258. Each of counter electrodes 256, reference electrode 258, and working electrodes 260 may be substantially similar to counter electrode 156, reference electrode 158, and working electrodes 160 described above with reference to FIG. 3A. Sensing portion 204 may be connected to a CGM housed within housing 202.

Delivery lumen 206 may be connected to an infusion set and/or an insulin pump housed within housing 202, and may be configured to deliver insulin via one or more apertures in fluid communication with a lumen of delivery lumen 206 and inserted within patient 112. In the example shown, delivery lumen 206 may output insulin at distal end 208.

Insulin excipient concentration may be greatest nearest the insulin delivery site and may decrease as the excipients diffuse within the patient. In some examples, insulin excipients may be deposited on one or more of counter electrodes 256, reference electrode 258, and working electrodes 260, e.g., if D is small enough such that the excipients concentration is high enough near those electrodes, and cause electrochemical interference.

In some examples, housing 202 may be configured to have a lateral separation distance D between sensing portion 204 and insulin delivery lumen 206 of 5 millimeters or greater. For example, housing 202 may be configured to have a separation distance D of 10 millimeters, or 11 millimeters, or greater. In some examples, separation distance D between sensing portion 204 and insulin delivery lumen 206 may be less than 5 millimeters.

In examples in which D is small enough such that insulin excipients may cause electrochemical interference, medical device 200 may be configured to determine the presence and/or amount of electrochemical interference. Medical device 200 may further be configured to output a signal, e.g., information indicative of the presence and/or amount of electrochemical interference, to another device, based on the determination of the presence and/or amount of electrochemical interference. In some examples, medical device 200 may be further configured to output an alert based on the determination of the presence and/or amount of electrochemical interference, and in some examples another device may be configured to output an alert based on the signal.

FIG. 4 is a circuit diagram illustrating an example electrical circuit model 400 of an electrochemical cell of monitoring device 100. Electrical circuit model 400 includes a resistor 402 approximating solution resistance (Rs), a resistor 404 approximating charge transfer resistance (Rct, e.g., the reciprocal of the charge transfer conductance Yct, namely, 1/Yct), a capacitor 406 approximating double layer capacitance 406 (Cdl), and expression 410 is an analytic expression for the impedance of an electrical current of electrical circuit model 400. In the example shown, resistor 402 is in series with a parallel combination of resistor 404 and capacitor 406, e.g., modeling the electrochemical cell as a solution resistance in series with a parallel combination of the double layer capacitance and a charge transfer resistance.

As described above, the accuracy of an electrical circuit model in approximating the actual physical structure and materials of electrical components of the electrochemical cell of monitoring device 100 may be sensitive to the choice of electrical circuit model components and their arrangement, and which measured impedance values (e.g., which frequencies and/or frequency ranges) are used in the determination and/or calculation. For example, electrical circuit model 400 approximates the electrical structure of the electrochemical cell as a resistor in series with a parallel combination of another resistor and a capacitor, and without any constant phase elements or a Warburg impedance. In some examples, including additional electrical circuit model components, such as a Warburg impedance or a constant phase element, in an electrical circuit model may result in a different calculation/result of one or more other electrical circuit model components (e.g., the solution resistance, charge transfer resistance, and/or double layer capacitance) as compared with electrical circuit model 400 based on the same electrical parameter measurements (e.g., impedance or EIS data). In some examples, electrical circuit model 400 simplifies determination of electrical circuit model components and improves the accuracy of determination of the presence and amount of electrochemical interference based on the determination of the electrical circuit model components based on measurement of electrical parameters (impedance) of the electrochemical cell.

Expression 410 is an example analytic relation between impedance and electrical circuit model components 402-406. In examples described herein, the presence and amount of electrochemical interference is determined based on electrical circuit model components 402-406 or changes to electrical circuit model components 402-406, which in turn are determined via measured impedances, e.g., at a first time and a second time.

Electrical circuit model components 402-406 may be determined, e.g., by processing circuitry such as measurement processor 132 and/or controller 136, via fewer than four impedance values corresponding to the impedance of the electrochemical circuit at fewer than four frequencies. For example, the solution resistance Rs (e.g., resistor 402) may be determined at a measured impedance at a relatively high frequency, e.g., a frequency of at least 1 kilohertz (kHz) and less than or equal to 8 kHz. In some examples, the solution resistance may be determined based on an impedance measured at a frequency higher than 8 kHz. In the example shown, the impedance of electrical circuit model 400 at a relatively high frequency is substantially the solution resistance, e.g., the charge transfer resistance is substantially close to zero at high frequencies and a good approximation of the solution resistance Rs is the real part of the measured impedance.

The charge transfer resistance Rct may be determined according to equation 1 below using impedance values at any frequency, where Im(Z) is the imaginary part of the impedance (e.g., the reactance), Re(Z) is the real part of the impedance, and tan phi is Im(Z)/Re(Z). It is often convenient to evaluate Rct at a relatively low frequency. For example, the charge transfer resistance Rct (e.g., resistor 404) may be determined at a measured impedance at a relatively low frequency, e.g., a frequency of at least 0.1 hertz (Hz) and less than or equal to 100 Hz. In some examples, the Rct may be determined based on an impedance measured at a frequency less than 0.1 Hz, although it may not be practical to do so, e.g., impedances at lower frequencies may take a prohibitively long time to measure. For example, the impedance of electrical circuit model 400 at low frequencies, e.g., less than 0.1 Hz, is substantially the addition of the solution resistance and the charge transfer resistance, however, it may take greater than 10 seconds to obtain a measurement. For example, the impedance may be measured with a periodic (e.g., often sinusoidal) input current signal, and it is often desirable to measure over several cycles, e.g., 3 or more cycles. A low frequency measurement at low frequencies less than 0.1 Hz may then take 30 seconds or more.

$$Rct = -\frac{Rs\left(1 + \left(\frac{\text{Im}(Z)}{Rs - \text{Re}(Z)}\right)^2\right)\tan\phi}{\tan\phi + \left(\frac{\text{Im}(Z)}{Rs - \text{Re}(Z)}\right)} \tag{1}$$

By way of conceptual description, at relatively high frequencies, electrical current follows the path of least resistance through capacitor 406, and the real part of the impedance is substantially equal to the resistance of resistor 402. At relatively low frequencies, e.g., approaching a frequency of zero or direct current (DC), electrical current cannot flow through capacitor 406 and follows a path including resistor 404, and the real part of the impedance at low frequencies is substantially equal to the addition of Rs and Rct.

In the example shown, the double layer capacitance Cdl (e.g., capacitor 406) may be determined based on the solution resistance Rs, the charge transfer resistance Rct (e.g., as 1/Yct or the reciprocal of the charge transfer conductance), and a measured impedance at a frequency at which the impedance phase is substantially negative 90 degrees. In some examples, the double layer capacitance Cdl may be determined using an impedance measured at any frequency according to equation 2 below, where ω is the angular frequency ω=2*pi*f, and f is the frequency (e.g., in hertz). In some examples, a frequency at which the impedance phase is substantially negative 90 degrees may be a relatively low frequency. For example, a capacitor has a phase of or about −90 degrees (e.g., the voltage lags the current by 90 degrees), and Cdl may be approximated as an ideal capacitor. As illustrated in the Bode plot of FIG. 5 below, the phase of the example measured impedance approaches −90 degrees as the frequency approaches zero. In some examples, Cdl may be determined using the same impedance used for determining the solution resistance. In other words, the electrical circuit model components Rs, Rct, and Cdl may be determined based on two measured impedance values, namely, the measured impedance corresponding to a relatively low frequency and the measured impedance corresponding to a relatively high frequency. In some examples, Cdl may be determined based on multiple impedance values measured at multiple frequencies.

$$Cdl = \frac{1}{\omega Rcl}\left(\frac{\text{Im}(Z)}{Rs - \text{Re}(Z)}\right) \tag{2}$$

In some examples, Cdl may be used to determine long-term or permanent changes to monitoring device 100. For example, processing circuitry may determine whether the performance and/or one or more electrical parameters (e.g., iSig 157) have changed based on Cdl. In some examples, processing circuitry may determine an amount of electrochemical interference, short-term or long-term, based on Cdl. An amount of electrochemical interference may include a change to the responsivity of the electrochemical cell of monitoring device 100, e.g., a bias or offset of iSig 157 relative to an initial condition or state of the electrochemical cell in the absence of electrochemical interference. For example, a change in iSig 157 may be due to electrochemical interference, the presence of an analyte such as glucose (e.g., a normal measurement), or both. Processing circuitry may be configured to determine an amount of signal contribution to iSig 157 from electrochemical interference based on Cdl or a change in Cdl. In some examples, monitoring device 100 and processing circuitry may be configured to determine a first Cdl at a first time based on a first set of measured EIS data (e.g., plurality of impedance measurements at a plurality of frequencies) and to determine a second Cdl at a second time after the first time and based on a second set of measured EIS. Processing circuitry may be configured to determine an amount of electrochemical interference based on a change between the first and second Cdl values from the first time to the second time.

In some examples, processing circuitry may be configured to compensate for electrochemical interference based on Cdl, e.g., to determine the amount of electrochemical interference and reconfigure configuration parameters of monitoring device 100 so as to determine or read glucose correctly in the presence of electrochemical interference.

Figure 5:
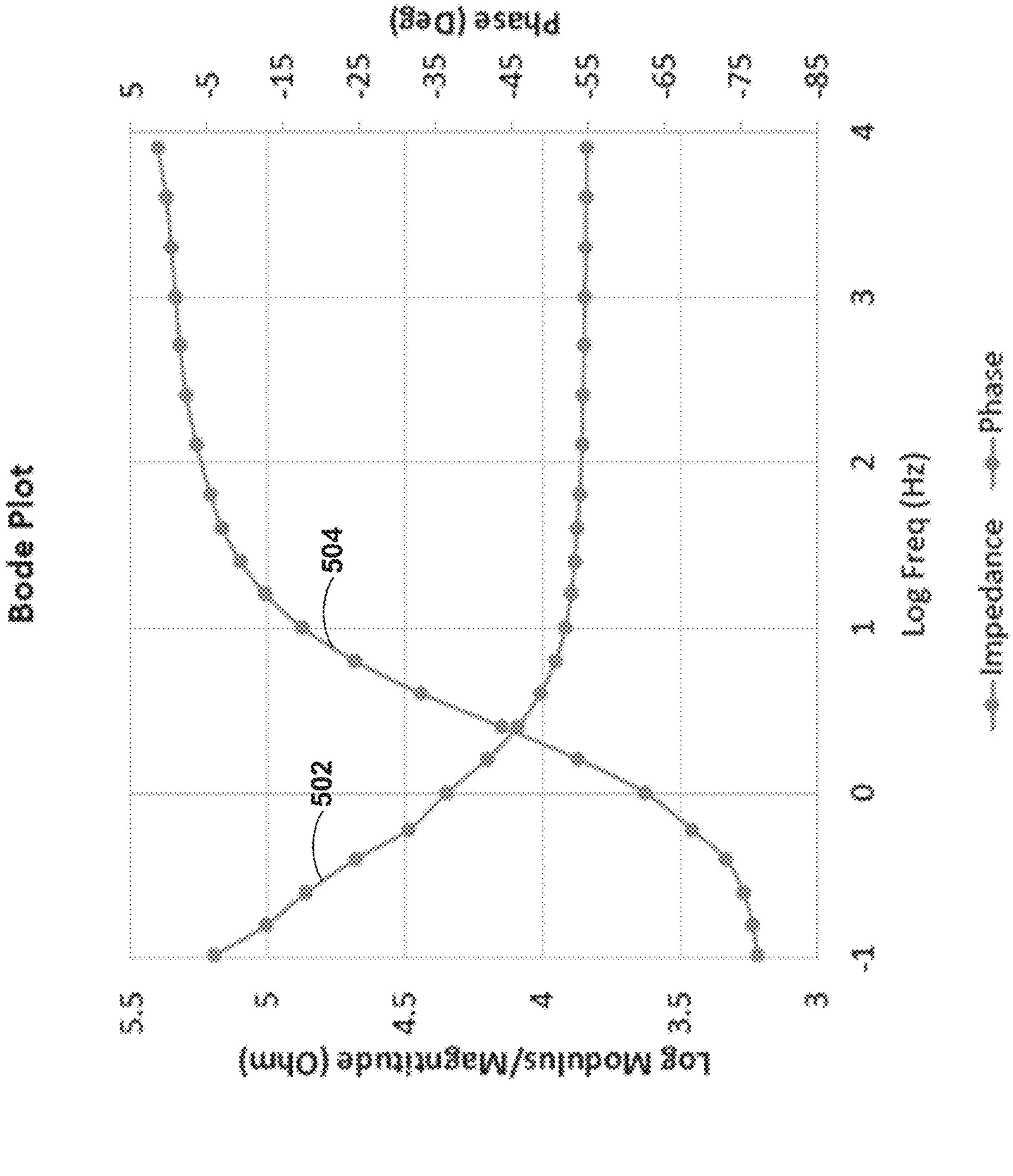
FIG. 5 is a Bode plot of example measured EIS data.

FIG. 5 is a Bode plot of example measured EIS data of an example monitoring device 100. In the example shown, plot 502 is the modulus of the impedance and plot 504 is the phase of the impedance. Plot 502 is a log-log plot, that is, the log of the modulus of the impedance is plotted versus the log of frequency, and plot 504 is the phase in degrees plotted versus the log of the frequency. In the example shown, as the frequency increases to relatively high frequencies, e.g., equal to or more than 1 kHz, the phase approaches zero degrees and the modulus approaches Rs. As the frequency decreases to relatively low frequencies, the phase approaches −90 degrees, and the modulus approaches Rs+Rct. In the example shown, the measured data does not include frequencies low enough to such that at the lowest frequency, the modulus of the impedance is substantially equal to Rs+Rct. As described above, Rct of electrical circuit model 400 may be determined based on measured impedances at lower frequencies than the example Bode plot, however, it may be impractical to do so, and equation 1 above may be used to determine Rct based on an impedance measured at any frequency. The lower the frequency of impedance measurement, the more accurate the results for Rct. Due to physical limitations of measurement, equation 1 may be used to estimate the value of Rct if data from sufficiently low frequencies are not available such that the Rs value can simply be subtracted from the impedance magnitude at said low frequency.

Figure 6B:
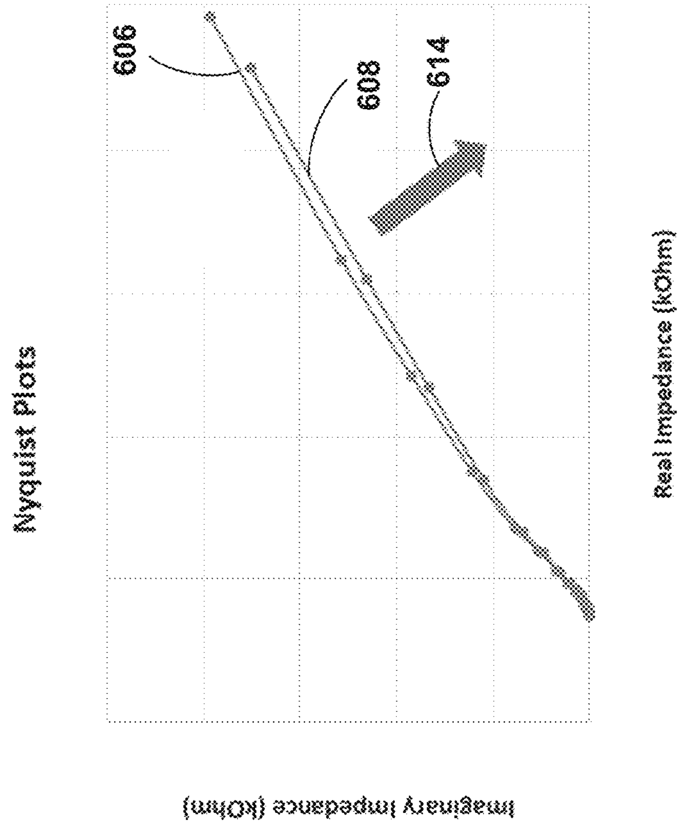
FIG. 6B is a Nyquist plot of another example of measured EIS data.
Figure 6A:
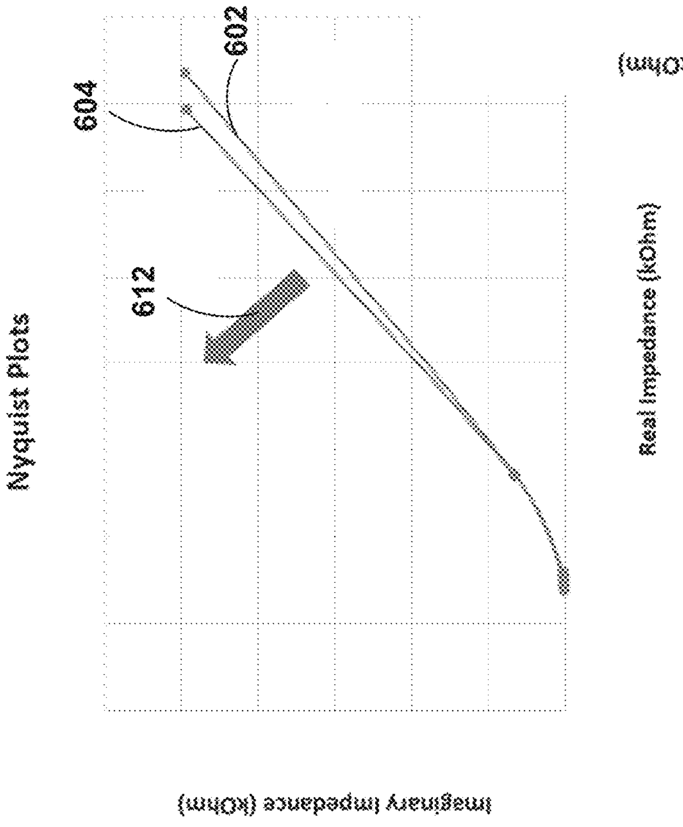
FIG. 6A is a Nyquist plot of an example of measured EIS data.

FIGS. 6A and 6B are a Nyquist plots of examples of measured EIS data. The example Nyquist plots 602 and 604 of FIG. 6A illustrate electrochemical interference caused by acetaminophen, and the example Nyquist plots 606 and 608 of FIG. 6B illustrate electrochemical interference caused by insulin excipients. In each of the plots 602-608 illustrated in FIGS. 6A and 6B, the EIS data is plotted as the imaginary part of the impedance versus the real part of the impedance for a plurality of impedances at a plurality of frequencies. The frequencies increase for each datapoint shown as the datapoints increase in both real and imaginary magnitude.

In the examples shown in FIG. 6A, electrochemical interference caused by acetaminophen causes an increase in the slope of the Nyquist plot of the EIS data relative to EIS data without interference. For example, Nyquist plot 602 is a plot of EIS data without electrochemical interference, and Nyquist plot 604 is a plot of the EIS data with electrochemical interference caused by acetaminophen, e.g., acetaminophen is added to a solution (e.g., such as interstitial fluid) before or while EIS data corresponding to plot 604 is measured. As illustrated by directional arrow 612, the presence of acetaminophen causes the Nyquist plot of the EIS data to increase in slope from the initial condition without interference (e.g., Nyquist plot 602) to an interference condition (e.g., Nyquist plot 604).

In the examples shown in FIG. 6B, electrochemical interference caused by insulin excipients causes a decrease in the slope of the Nyquist plot of the EIS data relative to EIS data without interference. As illustrated in FIG. 6B, Nyquist plot 606 is a plot of EIS data without electrochemical interference, and Nyquist plot 608 is a plot of the EIS data with electrochemical interference caused by insulin excipients, e.g., an insulin dose/bolus including insulin and insulin excipients is added to a solution (e.g., such as interstitial fluid) before or while EIS data corresponding to plot 608 is measured. In some examples, the EIS data corresponding to plots 602 and 606 may be the same EIS data, and plots 602 and 606 may be same. As illustrated by directional arrow 614, the presence of insulin excipients causes the Nyquist plot of the EIS data to decrease in slope from the initial condition without interference (e.g., Nyquist plot 606) to an interference condition (e.g., Nyquist plot 608).

In the examples shown, electrochemical interference caused by acetaminophen or insulin excipients are distinguishable from each other based on Nyquist slope. In the examples shown, electrochemical interference caused by acetaminophen or insulin excipients cause an opposite effect on the Nyquist slope of EIS data, and processing circuitry may determine whether electrochemical interference is caused by acetaminophen or insulin excipients based on Nyquist slope of measured EIS data, e.g., relative to a known or periodically audited non-interference measured EIS data.

Figures 7A, 7B, 7C:
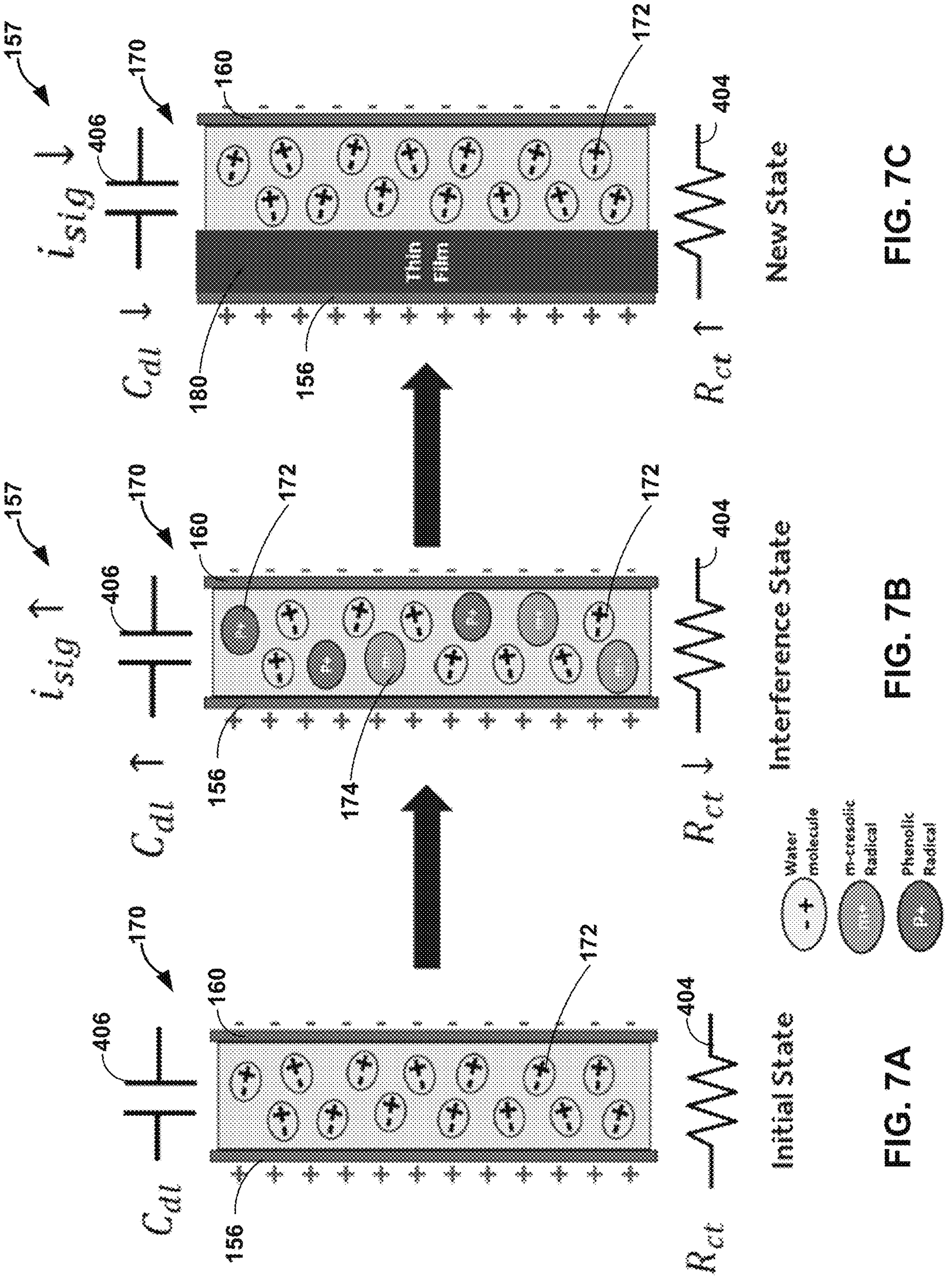
FIG. 7A is a cross-sectional view of a portion of an example electrochemical cell in an initial state.
FIG. 7B is a cross-sectional view of a portion of an example electrochemical cell in an interference state.
FIG. 7C is a cross-sectional view of a portion of an example electrochemical cell in a new state.

FIGS. 7A-7C illustrate the buildup of a thin film on an electrode of an electrochemical cell due to insulin excipients, and are described concurrently below. FIG. 7A is a cross-sectional view of a portion of an example electrochemical cell in an initial state, FIG. 7B is a cross-sectional view of a portion of an example electrochemical cell in an interference state, FIG. 7C is a cross-sectional view of a portion of an example electrochemical cell in a new state. In the examples shown, the new state illustrated in FIG. 7C may be a persistent, long-term, or permanent new state of the electrochemical cell.

In the example shown, the electrochemical cell of monitoring device 100 is in an initial state, and has a particular charge transfer resistance (and charge transfer conductance) and a particular double layer capacitance which may be approximated by the electrical circuit model components 404, 406, namely, charge transfer resistance resistor 404 and double layer capacitance capacitor 406. In operation without electrochemical interference, the electrochemical cell outputs iSig 157 in response to the presence and/or amount of an analyte within interstitial fluid 170, e.g., glucose. In the example shown, interstitial fluid 170 comprises mostly water, e.g., water molecules 172. In the example shown, iSig 157 (not shown in FIG. 7A) or changes to iSig 157 may be proportional to an amount of glucose present or changes to the amount of glucose present in interstitial fluid 170.

When a bolus of insulin is provided to the patient, e.g., via insulin pump 116, interstitial fluid 170 may contain insulin and insulin excipients such as phenol and m-cresol. When these interfering compounds come in contact with sensor electrodes, the bias voltage may cause them to oxidize to phenolic radicals 172 and m-cresolic radicals 174, as shown in FIG. 7B. As illustrated, the presence of phenolic radicals 172 and m-cresolic radicals 174 causes additional charge transfer to transfer to the sensor electrodes, which causes the charge transfer resistance 404 to reduce, the double layer capacitance 406 to increase, and iSig 157 to increase. Device 130 may sense iSig 157. In some examples, as insulin causes patient 112 to absorb the glucose, the glucose concentration within interstitial fluid 170 decreases, causing iSig 157 to decrease. However, the insulin excipients cause iSig 157 to increase (e.g., the electrochemical interference with the measurement of the analyte of interest). After a time, the phenolic radicals 172 and m-cresolic radicals 174 may electropolymerize and deposit on electrode 156 as illustrated in FIG. 7C, and/or on electrode 160 (not shown), and build up a thin film 180. Thin film 180 may change the electrical responsivity of the electrochemical cell. As illustrated in FIG. 7C, thin film 180 may cause the charge transfer resistance Rct of the electrochemical cell to increase, and the double layer capacitance of the electrochemical cell to decrease, changing the responsivity of the electrochemical cell to an analyte within solution 170. Namely, for the same concentration of an analyte, such as glucose, within solution 170, the signal response iSig 157 of the electrochemical cell including thin film 180 as illustrated in FIG. 7C will be less than the signal response iSig 157 of the electrochemical cell without thin film 180 as illustrated in FIG. 7A. In other words, the insulin excipients can cause both short term effects due to oxidation, and long term effects due to depositing as a thin film 180, which can change the long-term or permanent electrical configuration of the electrochemical cell, e.g., the insulin excipients cause long-term electrochemical interference illustrated in FIG. 7C, and insulin excipients in solution 170 cause short-term electrochemical interference as illustrated in FIG. 7B, e.g., while the insulin excipients remain in solution.

Figure 8:
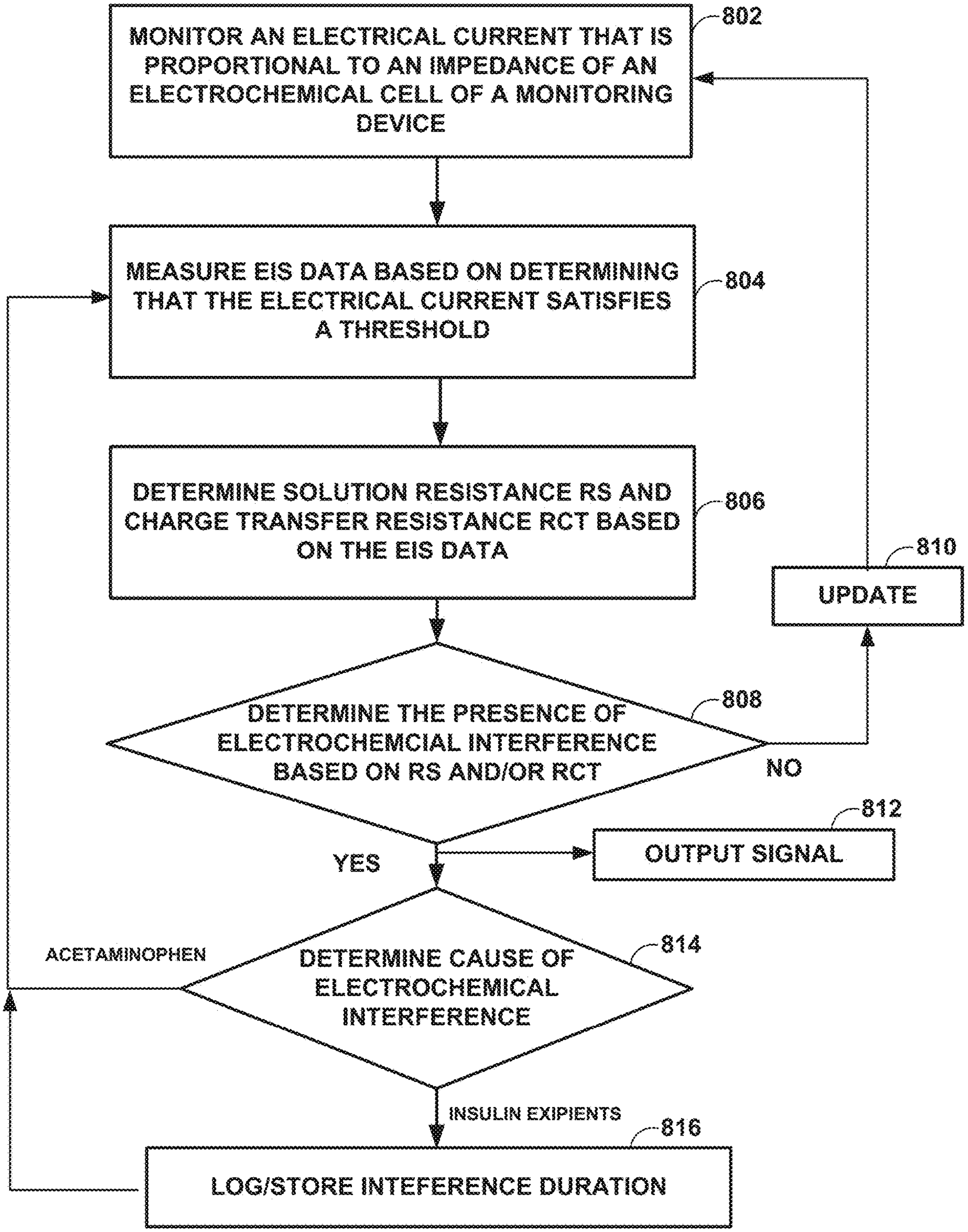
FIG. 8 is a flowchart illustrating an example method of determining electrochemical interference of an electrochemical cell.

FIG. 8 is a flowchart illustrating an example method of determining electrochemical interference of an electrochemical cell. Although the example technique of FIG. 8 is described with respect to system 110, monitoring device 100, and sensor electronics device 130 of FIGS. 1 and 2, the example technique of FIG. 8 may be performed with any type of monitoring device and/or glucose sensor, e.g., including processing circuitry such as measurement processor 132 and/or controller 136 configured to execute the technique. In some examples, the example technique of FIG. 8 may be performed by processing circuitry (e.g., measurement processor 132), configured to execute instructions stored in memory (e.g., memory 140), such as interference detection unit 142.

Measurement processor 132 monitors an electrical current that is proportional to an impedance of an electrochemical cell of monitoring device 100 (802). For example, measurement processor 132 may monitor iSig 157. Measurement processor 132 determines whether the electrical current satisfies a threshold, and measures a plurality of impedances of the electrochemical cell at a plurality of frequencies responsive to the electrical current satisfying the threshold (804). For example, measurement processor 132 may compare iSig 157 to an electrical current threshold stored in memory 140, and measurement processor may cause controller 136 to measure EIS data.

Measurement processor 132 determines a charge transfer conductance and a solution resistance based on the plurality of impedances at fewer than four of the corresponding plurality of frequencies (806). For example, as described above, measurement processor 132 may determine a solution resistance Rs component 402 of electrical circuit model 400 (e.g., as a model of the electrochemical cell of monitoring device 100) based on an impedance at a relatively high frequency, e.g., a frequency of at least 500 Hz, and the frequency may additionally be less than or equal to 8 kHz. Measurement processor 132 may determine a charge transfer conductance by determining its reciprocal, e.g., a charge transfer resistance Rct component 404 of electrical circuit model 400 based on Rs and an impedance at a relatively low frequency, e.g., a frequency less than or equal to 100 Hz. In some examples, measurement processor 132 may determine Rct based on Rs and a frequency that is additionally equal to or more than 0.1 Hz, e.g., in order to obtain an impedance value at a low enough frequency over a relatively short time with use of equation 1.

In some example, measurement processor 132 may also determine a Nyquist slope, e.g., based on the measured EIS data at (806). In other examples, measurement processor 132 may also determine the Nyquist slope after determining the presence of electrochemical interference, e.g., after (808) below.

Measurement processor 132 determines the presence of electrochemical interference based on the solution resistance and the charge transfer conductance (808). For example, measurement processor 132 may determine that electrochemical interference is present based on a change to the solution resistance Rs and/or charge transfer resistance Rct, e.g., by comparison to previously measured Rs, Rct values, or by comparison to a predetermined threshold Rs and/or Rct that may be stored in memory 140. In some examples, measurement processor 132 may determine the presence of electrochemical interference based on a rate of change of Rs and/or Rct. For example, if measurement processor 132 determines particular values for Rs and Rct based on the currently measured EIS data and those values, or changes to those values from previous values determined via previous EIS data do not satisfy a threshold, measurement processor 132 and may determine the presence of electrochemical interference based on a rate of change of Rs and/or Rct over time.

If measurement processor 132 determines that electrochemical interference is not present, or has not changed, at (808), measurement processor 132 may update any signal compensation information or configuration information of monitoring device 100 based on the currently measured EIS data and/or any determined quantities (such as Rs and Rct) at branch (810). The method may then proceed to (800) with measurement processor 132 continuing and/or resuming monitoring of the electrical current that is proportional to an impedance of the electrochemical cell.

If measurement processor 132 determines that electrochemical interference is present, or has changed, at (808), measurement processor 132 may output a signal (812). For example, measurement processor 132 may cause monitoring device to output a signal to patient device 124. Patient device 124 may be configured the receive the signal, and based on the signal, output an audible alert sound, output a visual alert indicator (e.g., such as activating or causing an LED to illuminate and/or flash), output information to a user interface, output a message to one or more device, and the like. In some examples, measurement processor 132 output a signal and monitoring device 100, medical device 200, or any other suitable device, may be configured to receive the signal, determine whether to cause an alert to be output based on the signal, and to output an audible alert sound, output a visual alert indicator, output information to a user interface, output a message to one or more device, and the like. In some examples, the signal may comprise information indicative of the presence and/or amount of electrochemical interference.

Measurement processor 132 determines a cause of the electrochemical interference (814). For example, measurement processor 132 may determine a Nyquist slope based on the measured EIS data and compare the slope, or a change or rate of change of the slope, with previously determined Nyquist slopes determined based on previously measured EIS data, or with a Nyquist slope threshold. Measurement processor 132 may determine that electrochemical interference is caused by acetaminophen based on determining an increased Nyquist slope (814), and measurement processor 132 may determine that electrochemical interference is caused by insulin excipients based on determining a decreased Nyquist slope (816).

Additionally, measurement processor 132 may determine an amount of electrochemical interference at (814). For example, measurement processor 132 may determine a double layer capacitance Cdl component 406 of the electrical circuit model 400 based on the solution resistance Rs, the charge transfer conductance Rct, and on an impedance value of the plurality of impedance values (e.g., the EIS data) corresponding to a frequency at which the impedance phase is substantially negative 90 degrees. In some examples, measurement processor 132 may determine an amount of electrochemical interference based on a change or rate of change of Cdl, e.g., based on Cdl values determined based on EIS data measured at different times. For example, measurement processor 132 may wait for a period time, cause controller 136 to measure a second set of EIS data, determine a second set of Rs, Rct, and Cdl values as described above, and determine an amount of electrochemical interference based on first and second double layer capacitance values.

If measurement processor 132 determines the cause of the electrochemical interference to be acetaminophen, the method may proceed to (804) and measurement processor 132 may measure a new plurality of impedances, e.g., a new EIS data set. For example, measurement processor 132 may operate in a loop between (804) and (814) until the acetaminophen concentration reduces such that it no longer causes interference. Measurement processor 132 may then determine that electrochemical interference is not present at (808) and continue at branch (810) as described above.

If measurement processor 132 determines the cause of the electrochemical interference to be insulin excipients, measurement processor 132 may determine and log or store a duration of the electrochemical interference (816). Additionally, measurement processor 132 may determine that the electrochemical interference is long-term, and determine compensation for the electrochemical interference, e.g., compensation for iSig 157 or the threshold comparator at (804), and/or electrical circuit model components Rs, Rct, Cdl, or any other configuration parameters of monitoring device 100. The method may then proceed to (804) and measurement processor 132 may measure a new plurality of impedances, e.g., a new EIS data set. For example, measurement processor 132 may operate in a loop between (804) and (816) until the insulin excipient concentration reduces such that it no longer causes interference, or until measurement processor 132 determines that long-term electrochemical interference is compensated for. For example, measurement processor 132 may implement the compensation at (804) such that a different iSig 157 no longer satisfies the threshold, or at (808) via electrical circuit model components such measurement processor 132 determines electrochemical interference is no longer present (e.g., via determining that it is compensated for), and the method may continue at branch (810) as described above.

Other illustrative examples of the disclosure are described below.

Example 1: A method includes monitoring, via a device including an electrochemical cell, an electrical current that is proportional to an impedance of the electrochemical cell; responsive to determining that the electrical current satisfies a threshold, measuring, via the device, a plurality of impedances of the electrochemical cell corresponding to a plurality of frequencies; determining a charge transfer conductance and a solution resistance based on the plurality of impedances at fewer than four of the corresponding plurality of frequencies; determining the presence of electrochemical interference based on the solution resistance and the charge transfer conductance; and outputting an alert based on the determination of the presence of electrochemical interference.

Example 2: The method of example 1, wherein determining the solution resistance comprises determining the solution resistance based on an impedance value of the plurality of impedance values corresponding to a relatively high frequency.

Example 3: The method of example 2, wherein the relatively high frequency comprises a frequency of at least 1 kilohertz (kHz) and less than or equal to 8 kHz.

Example 4: The method of any one of examples 1 through 3, wherein determining the charge transfer conductance comprises determining the charge transfer conductance based on the solution resistance and based on an impedance value of the plurality of impedance values corresponding to a relatively low frequency.

Example 5: The method of example 4, wherein the relatively low frequency comprises a frequency of at least 0.1 hertz (Hz) and less than or equal to 100 Hz.

Example 6: The method of any one of examples 1 through 5, further includes determining a double layer capacitance based on the solution resistance, the charge transfer conductance, and on an impedance value of the plurality of impedance values corresponding to a frequency at which the impedance phase is substantially negative 90 degrees.

Example 7: The method of example 6, further comprising determining an amount of electrochemical interference based on the double layer capacitance.

Example 8: The method of example 7, wherein the plurality of impedances corresponding to a plurality of frequencies is a first plurality of impedances measured at a first time, wherein the charge transfer conductance is a first charge transfer conductance, wherein the solution resistance is a first solution resistance, where the double layer capacitance is a first double layer capacitance, wherein determining the amount of electrochemical interference comprises: measuring, via the device, a second plurality of impedances of the electrochemical cell corresponding to the plurality of frequencies at a second time; and determining a second charge transfer conductance and a second solution resistance of the electrochemical cell based on the second plurality of impedances at fewer than four of the corresponding plurality of frequencies; determining a second double layer capacitance based on the second solution resistance, the second charge transfer conductance, and on the impedance value of the second plurality of impedance values corresponding to a frequency at which the impedance phase is substantially negative 90 degrees; and determining the amount of electrochemical interference based on the first double layer capacitance and the second double layer capacitance.

Example 9: The method of any one of examples 1 through 8, further includes determining a Nyquist slope; and determining whether the electrochemical interference is caused by at least one insulin excipient or acetaminophen based on the Nyquist slope.

Example 10: A device includes a glucose monitor; a memory; and one or more processors implemented in circuitry and in communication with the memory, the one or more processors configured to: monitor an electrical current that is proportional to an impedance of the glucose monitor; responsive to determining that the electrical current satisfies a threshold, receive one or more measurements of a plurality of impedances of the glucose monitor corresponding to a plurality of frequencies; determine a charge transfer conductance and a solution resistance of the glucose monitor based on the plurality of impedances at fewer than four of the corresponding plurality of frequencies; determine the presence of electrochemical interference based on the charge transfer conductance and the solution resistance; and output an alert based on the determination of the presence of electrochemical interference.

Example 11: The device of example 10, wherein the one or more processors are further configured to determine the solution resistance based on an impedance value of the plurality of impedance values corresponding to a relatively high frequency.

Example 12: The device of example 11, wherein the relatively high frequency comprises a frequency of at least 1 kilohertz (kHz) and less than or equal to 8 kHz.

Example 13: The device of any one of examples 10 through 12, wherein the one or more processors are further configured to determine the charge transfer conductance based on the solution resistance and based on an impedance value of the plurality of impedance values corresponding to a relatively low frequency.

Example 14: The device of example 13, wherein the relatively low frequency comprises a frequency of at least 0.1 hertz (Hz) and less than or equal to 100 Hz.

Example 15: The device of any one of examples 10 through 14, wherein the one or more processors are further configured to: determine a double layer capacitance based on the solution resistance, the charge transfer conductance, and on an impedance value of the plurality of impedance values corresponding to a frequency at which the impedance phase is substantially negative 90 degrees.

Example 16: The device of example 15, wherein the one or more processors are further configured to determine an amount of electrochemical interference based on the double layer capacitance.

Example 15: The device of example 16, wherein the plurality of impedances corresponding to a plurality of frequencies is a first plurality of impedances measured at a first time, wherein the charge transfer conductance is a first charge transfer conductance, wherein the solution resistance is a first solution resistance, where the double layer capacitance is a first double layer capacitance, wherein the one or more processors are further configured to: receive one or more measurements of a second plurality of impedances of the electrochemical cell corresponding to the plurality of frequencies at a second time; determine a second charge transfer conductance and a second solution resistance of the electrochemical cell based on the second plurality of impedances at fewer than four of the corresponding plurality of frequencies; determine a second double layer capacitance based on the second solution resistance, the second charge transfer conductance, and on the impedance value of the second plurality of impedance values corresponding to a frequency at which the impedance phase is substantially negative 90 degrees; and determine the amount of electrochemical interference based on the first double layer capacitance and the second double layer capacitance.

Example 18: The device of any one of examples 10 through 17, wherein the one or more processors are further configured to: determine a Nyquist slope; and determine whether the electrochemical interference is caused by at least one insulin excipient or acetaminophen based on the Nyquist slope.

Example 19: A non-transitory computer-readable storage medium having stored thereon instructions that, when executed, configure a processor to: monitor, via a device including an electrochemical cell, an electrical current that is proportional to an impedance of the electrochemical cell; responsive to determining that the electrical current satisfies a threshold, receive one or more measurements from the device of a plurality of impedances of the electrochemical cell corresponding to a plurality of frequencies; determine a charge transfer conductance and a solution resistance of the electrochemical cell based on the plurality of impedances at fewer than four of the corresponding plurality of frequencies; determine the presence of electrochemical interference based on the charge transfer conductance and the solution resistance; and output an alert based on the determination of the presence of electrochemical interference.

Example 20: The non-transitory computer-readable storage medium of example 19 having stored thereon further instructions that, when executed, configure a processor to: determine the solution resistance based on an impedance value of the plurality of impedance values corresponding to a relatively high frequency; and determine the charge transfer conductance based on the solution resistance and based on an impedance value of the plurality of impedance values corresponding to a relatively low frequency.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term “processor” or “processing circuitry” may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer-readable media may include non-transitory computer-readable storage media and transient communication media. Computer readable storage media, which is tangible and non-transitory, may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media. It should be understood that the term “computer-readable storage media” refers to physical storage media, and not signals, carrier waves, or other transient media.

Various examples have been described. These and other examples are within the scope of the following claims.

What is claimed is:

1. A method comprising: measuring, via a device comprising an electrochemical cell and a glucose monitor, an electrical current that is proportional to an impedance of the electrochemical cell, the electrical current representing a blood glucose level of a patient; responsive to determining that the electrical current satisfies a threshold, measuring, via the device, a plurality of impedances of the electrochemical cell corresponding to a plurality of frequencies; determining a charge transfer conductance based on a first impedance of the plurality of impedances corresponding to a frequency of at least 0.1 hertz (Hz) and less than or equal to 100 Hz; determining a solution resistance based on a second impedance of the plurality of impedances corresponding to a frequency greater than 500 Hz and less than or equal to 8 kilohertz (kHz); determining a non-constant phase double layer capacitance based on the solution resistance, the charge transfer conductance, and a third impedance of the plurality of impedances corresponding to a first frequency at which an impedance phase is negative 40 degrees to negative 90 degrees; determining a presence of electrochemical interference on the representation of the electrochemical cell of the blood glucose level of the patient based on the solution resistance, the charge transfer conductance, and the non-constant phase double layer capacitance; and controlling, via the glucose monitor, delivery of insulin to the patient based on the determination of the presence of electrochemical interference.

2. The method of claim 1, further comprising determining an amount of electrochemical interference based on the non-constant phase double layer capacitance.

3. The method of claim 2, wherein the plurality of impedances corresponding to a plurality of frequencies is a first plurality of impedances measured at a first time, wherein the charge transfer conductance is a first charge transfer conductance, wherein the solution resistance is a first solution resistance, wherein the non-constant phase double layer capacitance is a first non-constant phase double layer capacitance, wherein determining the amount of electrochemical interference comprises:

measuring, via the device, a second plurality of impedances of the electrochemical cell corresponding to the plurality of frequencies at a second time; and determining a second charge transfer conductance and a second solution resistance of the electrochemical cell based on the second plurality of impedances at fewer than four of the corresponding plurality of frequencies;

determining a second non-constant phase double layer capacitance based on the second solution resistance, the second charge transfer conductance, and on the impedance value of the second plurality of impedance values corresponding to a second frequency at which the impedance phase is in a range from negative 40 degrees to negative 90 degrees;

determining the amount of electrochemical interference based on the first non-constant phase double layer capacitance and the second non-constant phase double layer capacitance; and controlling delivery of insulin to the patient based on the amount of electrochemical interference.

4. The method of claim 1, further comprising:

determining a Nyquist slope; and determining whether the electrochemical interference is caused by at least one insulin excipient or acetaminophen based on the Nyquist slope.

5. The method of claim 1, wherein the signal comprises information indicative of an amount of electrochemical interference.

6. The method of claim 5, further comprising:

determining whether to cause an alert to be output based on the signal, wherein the alert comprises at least one of an audible alert sound, a visual alert indicator, or information configured to by displayed by a user interface.

7. The method of claim 1, wherein the device includes a delivery lumen configured to output insulin.

8. The method of claim 7, wherein the delivery lumen is separated from the electrochemical cell by less than 100 millimeters.

9. A non-transitory computer-readable storage medium having stored thereon instructions that, when executed, configure a processor to: measure, via a device comprising an electrochemical cell and a glucose monitor, an electrical current that is proportional to an impedance of the electrochemical cell, the electrical current representing a blood glucose level of a patient; responsive to determining that the electrical current satisfies a threshold, receive one or more measurements from the device of a plurality of impedances of the electrochemical cell corresponding to a plurality of frequencies; determine a charge transfer conductance based on a first impedance of the plurality of impedances corresponding to a frequency of at least 0.1 Hz and less than or equal to 100 Hz; determine a solution resistance of the electrochemical cell based on a second impedance of the plurality of impedances corresponding to a frequency greater than 500 Hz and less than or equal to 8 kHz; determine a non-constant phase double layer capacitance based on the solution resistance, the charge transfer conductance, and a third impedance of the plurality of impedances corresponding to a first frequency at which an impedance phase is in a range from negative 40 degrees to negative 90 degrees; determine a presence of electrochemical interference on the representation of the electrochemical cell of the blood glucose level of the patient based on the charge transfer conductance, the solution resistance, and the non-constant phase double layer capacitance; and control, via the glucose monitor, delivery of insulin to the patient based on the determination of the presence of electrochemical interference.

10. A device comprising: a glucose monitor; a memory; and one or more processors implemented in circuitry and in communication with the memory, the one or more processors configured to: measure an electrical current that is proportional to an impedance of the glucose monitor; responsive to determining that the electrical current satisfies a threshold, receive one or more measurements of a plurality of impedances of the glucose monitor corresponding to a plurality of frequencies; determine a charge transfer conductance based on a first impedance of the plurality of impedances corresponding to a frequency of at least 0.1 Hz and less than or equal to 100 Hz; determine a solution resistance of the glucose monitor based on a second impedance of the plurality of impedances corresponding to a frequency greater than 500 Hz and less than or equal to 8 kilohertz (kHz); determine a non-constant phase double layer capacitance based on the solution resistance, the charge transfer conductance, and a third impedance of the plurality of impedances corresponding to a first frequency at which an impedance phase is in a range from negative 40 degrees to negative 90 degrees; determine a presence of electrochemical interference on the glucose monitor based on the charge transfer conductance, the solution resistance, and the non-constant phase double layer capacitance; and control, via the glucose monitor, delivery of insulin to the patient based on the determination of the presence of electrochemical interference.

11. The device of claim 10, wherein the one or more processors are further configured to determine an amount of electrochemical interference based on the non-constant phase double layer capacitance.

12. The device of claim 11, wherein the plurality of impedances corresponding to a plurality of frequencies is a first plurality of impedances measured at a first time, wherein the charge transfer conductance is a first charge transfer conductance, wherein the solution resistance is a first solution resistance, wherein the non-constant phase double layer capacitance is a first non-constant phase double layer capacitance, wherein the one or more processors are further configured to:

receive one or more measurements of a second plurality of impedances of the electrochemical cell corresponding to the plurality of frequencies at a second time;

determine a second charge transfer conductance and a second solution resistance of the electrochemical cell based on the second plurality of impedances at fewer than four of the corresponding plurality of frequencies;

determine a second non-constant phase double layer capacitance based on the second solution resistance, the second charge transfer conductance, and on the impedance value of the second plurality of impedance values corresponding to a second frequency at which the impedance phase is within a range from negative 40 degrees to negative 90 degrees;

determine the amount of electrochemical interference based on the first non-constant phase double layer capacitance and the second non-constant phase double layer capacitance; and control delivery of insulin to the patient based on the amount of electrochemical interference.

13. The device of claim 10, wherein the one or more processors are further configured to:

determine a Nyquist slope; and determine whether the electrochemical interference is caused by at least one insulin excipient or acetaminophen based on the Nyquist slope.

14. The method of claim 9, wherein the signal comprises information indicative of an amount of electrochemical interference.

* * * * *